United States Patent
Heil et al.

(10) Patent No.: US 10,646,379 B2
(45) Date of Patent: May 12, 2020

(54) INCONTINENCE DETECTION APPARATUS HAVING DISPLACEMENT ALERT

(71) Applicant: Hill-Rom Services, Inc., Batesville, IN (US)

(72) Inventors: Thomas F. Heil, Batesville, IN (US); Steven A. Dixon, Cincinnati, OH (US); Laetitia Gazagnes, Montpellier (FR); Timothy A. Lane, Greensburg, IN (US); David L. Ribble, Indianapolis, IN (US); Varad N. Srivastava, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 59 days.

(21) Appl. No.: 15/257,301

(22) Filed: Sep. 6, 2016

(65) Prior Publication Data

US 2016/0374626 A1     Dec. 29, 2016

Related U.S. Application Data

(63) Continuation of application No. 14/186,522, filed on Feb. 21, 2014, now abandoned.

(Continued)

(51) Int. Cl.
*A61F 13/42* (2006.01)
*A61B 5/00* (2006.01)
(Continued)

(52) U.S. Cl.
CPC .............. *A61F 13/42* (2013.01); *A61B 5/202* (2013.01); *A61B 5/6892* (2013.01); *A61B 5/74* (2013.01);
(Continued)

(58) Field of Classification Search
None
See application file for complete search history.

(56) References Cited

U.S. PATENT DOCUMENTS

| | | |
|---|---|---|
| 1,772,232 A | 8/1930 | Guilder |
| 2,127,538 A | 8/1938 | Seiger |
| (Continued) | | |

FOREIGN PATENT DOCUMENTS

| | | |
|---|---|---|
| CA | 2361145 | 12/1999 |
| CA | 2494896 | 12/1999 |
| (Continued) | | |

OTHER PUBLICATIONS

International Search Report, dated Sep. 15, 2014, on PCT/US2014/024214, filed on Mar. 12, 2014, 17 pages.

(Continued)

*Primary Examiner* — Curtis A Kuntz
*Assistant Examiner* — Shawna M Kingston
(74) *Attorney, Agent, or Firm* — Barnes & Thornburg LLP

(57) ABSTRACT

One embodiment of a method of interrogating a sensor to detect the presence of moisture on an occupant support comprises the steps of A) providing a moisture responsive sensor in a surveillance zone of the occupant support, the sensor being tuned to a center frequency; B) exciting the sensor with an electromagnetic signal having a frequency approximately equal to the center frequency; C) monitoring for a center frequency response from the sensor; D) comparing the center frequency response to an expected center frequency response; and E) if the center frequency response compares favorably to an expected center frequency response, issuing a first output consistent with the favorable comparison.

18 Claims, 24 Drawing Sheets

Related U.S. Application Data

(60) Provisional application No. 61/778,830, filed on Mar. 13, 2013.

(51) Int. Cl.
  *A61B 5/20* (2006.01)
  *G06K 7/10* (2006.01)
  *A61G 7/05* (2006.01)
  *A61G 7/02* (2006.01)

(52) U.S. Cl.
  CPC .......... *A61G 7/05* (2013.01); *G06K 7/10366* (2013.01); *A61F 2013/424* (2013.01); *A61G 7/02* (2013.01)

(56) References Cited

U.S. PATENT DOCUMENTS

| | | |
|---|---|---|
| 2,644,050 A | 6/1953 | Seiger |
| 2,668,202 A | 2/1954 | Kaplan |
| 2,726,294 A | 12/1955 | Kroening et al. |
| 2,907,841 A | 10/1959 | Campbell |
| 3,199,095 A | 8/1965 | Ashida |
| 3,696,357 A * | 10/1972 | Kilgore ............ A61F 5/48 128/886 |
| 3,971,371 A | 7/1976 | Bloom |
| 4,069,817 A | 1/1978 | Fenole et al. |
| 4,106,001 A | 8/1978 | Mahoney |
| 4,163,449 A | 8/1979 | Regal |
| 4,191,950 A | 3/1980 | Levin et al. |
| 4,212,295 A | 7/1980 | Snyder |
| 4,228,426 A | 10/1980 | Robert |
| 4,347,503 A | 8/1982 | Uyehara |
| 4,539,559 A | 9/1985 | Kelly et al. |
| 4,747,166 A | 5/1988 | Kuntz |
| 4,965,554 A | 10/1990 | Darling |
| 5,081,422 A | 1/1992 | Shih |
| 5,086,291 A | 2/1992 | Schwab, Jr. |
| 5,137,033 A | 8/1992 | Norton |
| 5,144,284 A | 9/1992 | Hammett |
| 5,291,181 A | 3/1994 | De Ponte |
| 5,438,721 A | 8/1995 | Pahno et al. |
| 5,459,452 A | 10/1995 | DePonte |
| 5,491,609 A | 2/1996 | Dankman et al. |
| 5,537,095 A | 7/1996 | Dick et al. |
| 5,675,854 A | 10/1997 | Zibelin |
| 5,760,694 A | 6/1998 | Nissim et al. |
| 5,790,035 A | 8/1998 | Ho |
| 5,824,883 A | 10/1998 | Park et al. |
| 5,910,080 A | 6/1999 | Selton |
| 5,947,943 A | 9/1999 | Lee |
| 6,028,241 A | 2/2000 | Armstead |
| 6,047,419 A | 4/2000 | Ferguson |
| 6,104,311 A | 8/2000 | Lastinger |
| 6,292,102 B1 | 9/2001 | Smith |
| 6,340,932 B1 | 1/2002 | Rodgers et al. |
| 6,341,393 B1 | 1/2002 | Votel |
| 6,351,215 B2 | 2/2002 | Rodgers et al. |
| 6,362,737 B1 | 3/2002 | Rodgers et al. |
| 6,384,728 B1 | 5/2002 | Kanor et al. |
| 6,544,200 B1 | 4/2003 | Smith et al. |
| 6,552,661 B1 | 4/2003 | Lastinger et al. |
| 6,583,722 B2 | 6/2003 | Jeutter et al. |
| 6,603,403 B2 | 8/2003 | Jeutter et al. |
| 6,621,410 B1 | 9/2003 | Lastinger et al. |
| 6,639,517 B1 | 10/2003 | Chapman et al. |
| 6,774,800 B2 | 8/2004 | Friedman et al. |
| 6,831,562 B2 | 12/2004 | Rodgers et al. |
| 6,832,507 B1 | 12/2004 | van de Berg et al. |
| 6,933,849 B2 | 8/2005 | Sawyer |
| 6,948,205 B2 | 9/2005 | Van Der Wurf et al. |
| 6,982,646 B2 | 1/2006 | Rodgers et al. |
| 7,017,213 B2 | 3/2006 | Chisari |
| 7,030,731 B2 | 4/2006 | Lastinger et al. |
| 7,071,830 B2 | 7/2006 | Sahlberg et al. |
| 7,120,952 B1 | 10/2006 | Bass et al. |
| 7,181,206 B2 | 2/2007 | Pedersen |
| 7,250,547 B1 | 7/2007 | Hofmeister et al. |
| 7,253,729 B2 | 8/2007 | Lastinger et al. |
| 7,274,944 B2 | 9/2007 | Lastinger et al. |
| 7,302,278 B2 | 11/2007 | Lastinger et al. |
| 7,305,246 B2 | 12/2007 | Lastinger et al. |
| 7,308,270 B2 | 12/2007 | Lastinger et al. |
| 7,348,930 B2 | 3/2008 | Lastinger et al. |
| 7,349,701 B2 | 3/2008 | Lastinger et al. |
| 7,355,090 B2 | 4/2008 | Ales, III et al. |
| 7,359,675 B2 | 4/2008 | Lastinger et al. |
| 7,400,860 B2 | 7/2008 | Lastinger et al. |
| 7,424,298 B2 | 9/2008 | Lastinger et al. |
| 7,489,252 B2 | 2/2009 | Long et al. |
| 7,489,282 B2 | 2/2009 | Lastinger et al. |
| 7,498,478 B2 | 3/2009 | Long et al. |
| 7,551,089 B2 | 6/2009 | Sawyer |
| 7,586,385 B2 | 9/2009 | Rokhsaz |
| 7,595,743 B1 | 9/2009 | Long et al. |
| 7,595,756 B2 | 9/2009 | Lastinger et al. |
| 7,598,853 B2 | 10/2009 | Becker et al. |
| 7,598,862 B2 | 10/2009 | Lastinger et al. |
| 7,599,699 B2 | 10/2009 | Lastinger et al. |
| 7,616,959 B2 | 11/2009 | Spenik et al. |
| 7,633,378 B2 | 12/2009 | Rodgers et al. |
| 7,649,125 B2 | 1/2010 | Ales, III et al. |
| 7,663,483 B2 | 2/2010 | Spenik et al. |
| 7,667,600 B2 | 2/2010 | Woodbury et al. |
| 7,812,731 B2 | 10/2010 | Bunza et al. |
| 7,822,386 B2 | 10/2010 | Lastinger et al. |
| 7,834,234 B2 | 11/2010 | Roe et al. |
| 7,834,235 B2 | 11/2010 | Long et al. |
| 7,834,765 B2 | 11/2010 | Sawyer |
| 7,834,766 B2 | 11/2010 | Sawyer |
| 7,838,720 B2 | 11/2010 | Roe et al. |
| 7,849,544 B2 | 12/2010 | Flocard et al. |
| 7,873,319 B2 | 1/2011 | Lastinger et al. |
| 7,977,529 B2 | 7/2011 | Bergman et al. |
| 8,009,646 B2 | 8/2011 | Lastinger et al. |
| 8,073,386 B2 | 12/2011 | Pedersen |
| 8,081,043 B2 | 12/2011 | Rokhsaz |
| 8,102,254 B2 | 1/2012 | Becker et al. |
| 8,104,126 B2 | 1/2012 | Caminade et al. |
| 8,106,782 B2 | 1/2012 | Fredriksson et al. |
| 8,111,165 B2 | 2/2012 | Ortega et al. |
| 8,111,678 B2 | 2/2012 | Lastinger et al. |
| 8,121,856 B2 | 2/2012 | Huster et al. |
| 8,181,290 B2 | 5/2012 | Brykalski et al. |
| 8,191,187 B2 | 6/2012 | Brykalski et al. |
| 8,196,809 B2 | 6/2012 | Thorstensson |
| 8,237,572 B2 | 8/2012 | Clement et al. |
| 8,248,249 B2 | 8/2012 | Clement et al. |
| 8,270,383 B2 | 8/2012 | Lastinger et al. |
| 8,279,069 B2 | 10/2012 | Sawyer |
| 8,319,633 B2 | 11/2012 | Becker et al. |
| 8,325,695 B2 | 12/2012 | Lastinger et al. |
| 8,332,975 B2 | 12/2012 | Brykalski et al. |
| 8,345,651 B2 | 1/2013 | Lastinger et al. |
| 8,395,014 B2 | 3/2013 | Helmer et al. |
| 8,428,039 B2 | 4/2013 | Lastinger et al. |
| 8,428,605 B2 | 4/2013 | Pedersen et al. |
| 8,461,982 B2 | 6/2013 | Becker et al. |
| 8,482,305 B2 | 7/2013 | Johnson |
| 8,487,774 B2 | 7/2013 | Reeder et al. |
| 8,502,684 B2 | 8/2013 | Bunza et al. |
| 8,628,506 B2 | 1/2014 | Ales, III et al. |
| 8,674,826 B2 | 3/2014 | Becker et al. |
| 8,742,929 B2 | 6/2014 | Sawyer |
| 8,749,319 B2 | 6/2014 | Rokhsaz et al. |
| 8,766,804 B2 | 7/2014 | Reeder et al. |
| 8,842,013 B2 | 9/2014 | Sawyer |
| 8,855,089 B2 | 10/2014 | Lastinger et al. |
| 8,866,615 B2 | 10/2014 | Sawyer |
| 8,878,557 B2 | 11/2014 | Kristiansen et al. |
| 8,878,676 B2 | 11/2014 | Koblasz |
| 8,896,449 B2 | 11/2014 | Sawyer |
| 8,914,923 B2 | 12/2014 | Smith |
| 8,933,292 B2 | 1/2015 | Abraham et al. |

(56) References Cited

U.S. PATENT DOCUMENTS

| | | | |
|---|---|---|---|
| 8,962,909 B2 | 2/2015 | Groosman et al. | |
| 9,048,819 B2 | 6/2015 | Rokhsaz et al. | |
| 9,107,776 B2 | 8/2015 | Bergman et al. | |
| 2002/0011932 A1 | 1/2002 | Rodgers et al. | |
| 2002/0033757 A1 | 3/2002 | Rodgers et al. | |
| 2002/0145526 A1* | 10/2002 | Friedman | A61B 5/0002 340/573.5 |
| 2003/0030568 A1 | 2/2003 | Lastinger et al. | |
| 2005/0003763 A1 | 1/2005 | Lastinger et al. | |
| 2005/0003865 A1 | 1/2005 | Lastinger et al. | |
| 2005/0052282 A1 | 3/2005 | Rodgers et al. | |
| 2005/0060246 A1 | 3/2005 | Lastinger et al. | |
| 2005/0174246 A1 | 8/2005 | Picco et al. | |
| 2005/0242946 A1 | 11/2005 | Hubbard, Jr. et al. | |
| 2005/0250453 A1 | 11/2005 | Lastinger et al. | |
| 2005/0277441 A1 | 12/2005 | Lastinger et al. | |
| 2005/0282545 A1 | 12/2005 | Lastinger et al. | |
| 2005/0282553 A1 | 12/2005 | Lastinger et al. | |
| 2006/0000285 A1* | 1/2006 | Edmonson | G01N 29/022 73/649 |
| 2006/0164320 A1 | 7/2006 | Lastinger et al. | |
| 2006/0270351 A1 | 11/2006 | Lastinger et al. | |
| 2007/0159332 A1 | 7/2007 | Koblasz | |
| 2007/0202809 A1 | 8/2007 | Lastinger et al. | |
| 2007/0270774 A1 | 11/2007 | Bergman et al. | |
| 2008/0116990 A1 | 5/2008 | Rokhsaz | |
| 2008/0262376 A1 | 10/2008 | Price | |
| 2008/0263776 A1 | 10/2008 | O'Reagan et al. | |
| 2008/0300559 A1 | 12/2008 | Gustafson et al. | |
| 2009/0160648 A1 | 6/2009 | Rokhsaz | |
| 2009/0289743 A1 | 11/2009 | Rokhsaz | |
| 2009/0292265 A1 | 11/2009 | Helmer et al. | |
| 2009/0315728 A1 | 12/2009 | Ales, III et al. | |
| 2009/0326417 A1 | 12/2009 | Ales, III et al. | |
| 2010/0043143 A1 | 2/2010 | O'Reagan et al. | |
| 2010/0145294 A1* | 6/2010 | Song | A61F 13/42 604/361 |
| 2011/0025458 A1 | 2/2011 | Rokhsaz et al. | |
| 2011/0025473 A1 | 2/2011 | Rokhsaz et al. | |
| 2011/0092890 A1 | 4/2011 | Stryker et al. | |
| 2011/0115635 A1 | 5/2011 | Petrovski et al. | |
| 2011/0263952 A1 | 10/2011 | Bergman et al. | |
| 2011/0283459 A1 | 11/2011 | Essers | |
| 2011/0291810 A1 | 12/2011 | Rokhsaz et al. | |
| 2011/0295619 A1 | 12/2011 | Tough | |
| 2011/0300808 A1 | 12/2011 | Rokhsaz et al. | |
| 2011/0302720 A1 | 12/2011 | Yakam et al. | |
| 2011/0309937 A1* | 12/2011 | Bunza | A61B 5/202 340/573.5 |
| 2012/0092027 A1 | 4/2012 | Forster | |
| 2012/0105233 A1 | 5/2012 | Bobey et al. | |
| 2012/0119912 A1 | 5/2012 | Ortega et al. | |
| 2012/0130330 A1 | 5/2012 | Wilson et al. | |
| 2012/0165772 A1 | 6/2012 | Groosman et al. | |
| 2012/0216607 A1 | 8/2012 | Sjöholm et al. | |
| 2012/0217311 A1 | 8/2012 | Rokhsaz et al. | |
| 2012/0268278 A1 | 10/2012 | Lewis et al. | |
| 2013/0019405 A1 | 1/2013 | Flanagan et al. | |
| 2013/0079590 A1 | 3/2013 | Bengtson | |
| 2013/0109929 A1 | 5/2013 | Menzel | |
| 2013/0123726 A1 | 5/2013 | Yu et al. | |
| 2013/0254141 A1 | 9/2013 | Barda et al. | |
| 2014/0120836 A1 | 5/2014 | Rokhsaz et al. | |
| 2014/0148772 A1 | 5/2014 | Hu et al. | |
| 2014/0152442 A1 | 6/2014 | Li | |
| 2014/0200538 A1 | 7/2014 | Euliano et al. | |
| 2014/0236629 A1 | 8/2014 | Kim et al. | |
| 2014/0244644 A1 | 8/2014 | Mashinchi et al. | |
| 2014/0247125 A1 | 9/2014 | Barsky | |
| 2014/0266735 A1 | 9/2014 | Riggio et al. | |
| 2014/0296808 A1 | 10/2014 | Curran et al. | |
| 2014/0358099 A1 | 12/2014 | Durgin et al. | |
| 2015/0080819 A1 | 3/2015 | Charna et al. | |
| 2015/0080834 A1 | 3/2015 | Mills | |
| 2015/0087935 A1 | 3/2015 | Davis et al. | |

FOREIGN PATENT DOCUMENTS

| | | |
|---|---|---|
| CN | 101304715 A | 11/2008 |
| CN | 102568259 | 7/2012 |
| CN | 202711437 | 1/2013 |
| CN | 102985853 | 3/2013 |
| DE | 4137631 | 5/1992 |
| DE | 69906388 | 2/2004 |
| DE | 69915370 | 3/2005 |
| DE | 69917491 | 5/2005 |
| DE | 60016946 | 6/2006 |
| DE | 102007050074 | 4/2009 |
| EP | 0335279 | 10/1989 |
| EP | 1286179 | 12/1999 |
| EP | 1147603 | 10/2001 |
| EP | 1149305 | 10/2001 |
| EP | 1153317 | 11/2001 |
| EP | 1218771 | 7/2002 |
| EP | 1153317 | 3/2003 |
| EP | 1147603 | 3/2004 |
| EP | 1410353 | 4/2004 |
| EP | 1149305 | 5/2004 |
| EP | 1218771 | 12/2004 |
| EP | 1684615 | 8/2006 |
| EP | 2014267 | 6/2007 |
| EP | 1868553 | 12/2007 |
| EP | 1897278 | 3/2008 |
| EP | 1959900 | 8/2008 |
| EP | 1994650 | 11/2008 |
| EP | 2019659 | 2/2009 |
| EP | 1410353 | 12/2009 |
| EP | 1897278 | 1/2010 |
| EP | 1684615 | 2/2010 |
| EP | 2156222 | 2/2010 |
| EP | 2313044 | 4/2011 |
| EP | 2579069 | 6/2011 |
| EP | 2444039 | 8/2011 |
| EP | 1959900 | 2/2012 |
| EP | 2738748 | 4/2012 |
| EP | 2452183 | 5/2012 |
| EP | 2496197 | 9/2012 |
| EP | 1994650 | 12/2012 |
| EP | 2542200 | 1/2013 |
| EP | 2548473 A2 | 1/2013 |
| EP | 2579069 | 4/2013 |
| EP | 2582341 | 4/2013 |
| EP | 2542200 | 2/2014 |
| EP | 2729107 | 5/2014 |
| EP | 2738748 | 6/2014 |
| EP | 2739254 | 6/2014 |
| EP | 2156222 | 8/2015 |
| EP | 2496197 | 8/2015 |
| EP | 2019659 | 4/2016 |
| EP | 2582341 | 4/2016 |
| EP | 2739254 | 11/2016 |
| GB | 145859 | 3/1919 |
| GB | 2145859 | 4/1985 |
| GB | 2408204 | 11/2003 |
| WO | WO 89/10110 | 4/1989 |
| WO | WO 94/20002 | 3/1994 |
| WO | WO 00/44091 | 7/2000 |
| WO | WO 01/25817 | 4/2001 |
| WO | WO 02/103645 | 12/2002 |
| WO | WO 2006/108540 | 10/2006 |
| WO | WO 2007/069968 | 6/2007 |
| WO | WO 2008/130298 | 10/2008 |
| WO | WO 2010/001271 | 1/2010 |
| WO | WO 2010/043368 | 4/2010 |
| WO | 2011043724 A1 | 4/2011 |
| WO | WO 2011/107580 | 9/2011 |
| WO | WO 2012/136157 | 10/2012 |
| WO | WO 2014/165041 | 3/2014 |
| WO | PCT/US2014/055066 | 9/2014 |

(56) References Cited

FOREIGN PATENT DOCUMENTS

WO    WO 2014/165041    10/2014
WO    WO 2015/137999    9/2015

OTHER PUBLICATIONS

PCT Search Report and Written Opinion, International Application No. PCT/US 14/55066, dated Mar. 9, 2015, 11 pages.
Response to Official Action, submitted Jun. 3, 2015, in European Patent Application No. 12177071.3, 14 pages.
U.S. Appl. No. 61/778,830, filed Mar. 13, 2013, 111 pages.
U.S. Appl. No. 61/899,655, filed Nov. 4, 2013, 105 pages.
International Search Report, dated Mar. 12, 2014, on PCT/US2014/024214, 137 pages.
First Office Action and its English Translation for Chinese Patent Application No. 201480078481.6 dated May 22, 2008; 26 pages.
Extended EP Search Report for European Patent Application No. 14885467.2 dated Feb. 28, 2017; 10 pages.
Communication Pursuant to Article 94(3) EPC for European Patent Application No. 14885467.2 dated Apr. 4, 2018; 6 pages.
Extended EP Search Report for European Patent Application No. 14778216.3 dated Apr. 29, 2016; 6 pages.
Communication pursuant to Article 94(3) EPC from the European Patent Office for European Patent Application No. 14885467.2, dated Jun. 25, 2019; 6 pages.

\* cited by examiner

| EXCITATION FREQUENCY YIELDING STRONG RSSI | FLUID IDENTITY AND/OR PROPERTIES |
|---|---|
| $f_{T+n}$ | |
| ⋮ | |
| $f_{T+2}$ | VOMIT |
| $f_{T+1}$ | BLOOD |
| $f_C$ | NO FLUID |
| $f_{T-1}$ | URINE — ACIDIC |
| $f_{T-2}$ | URINE — ALKALINE |
| ⋮ | |
| $f_{T-n}$ | |

*FIG. 11*

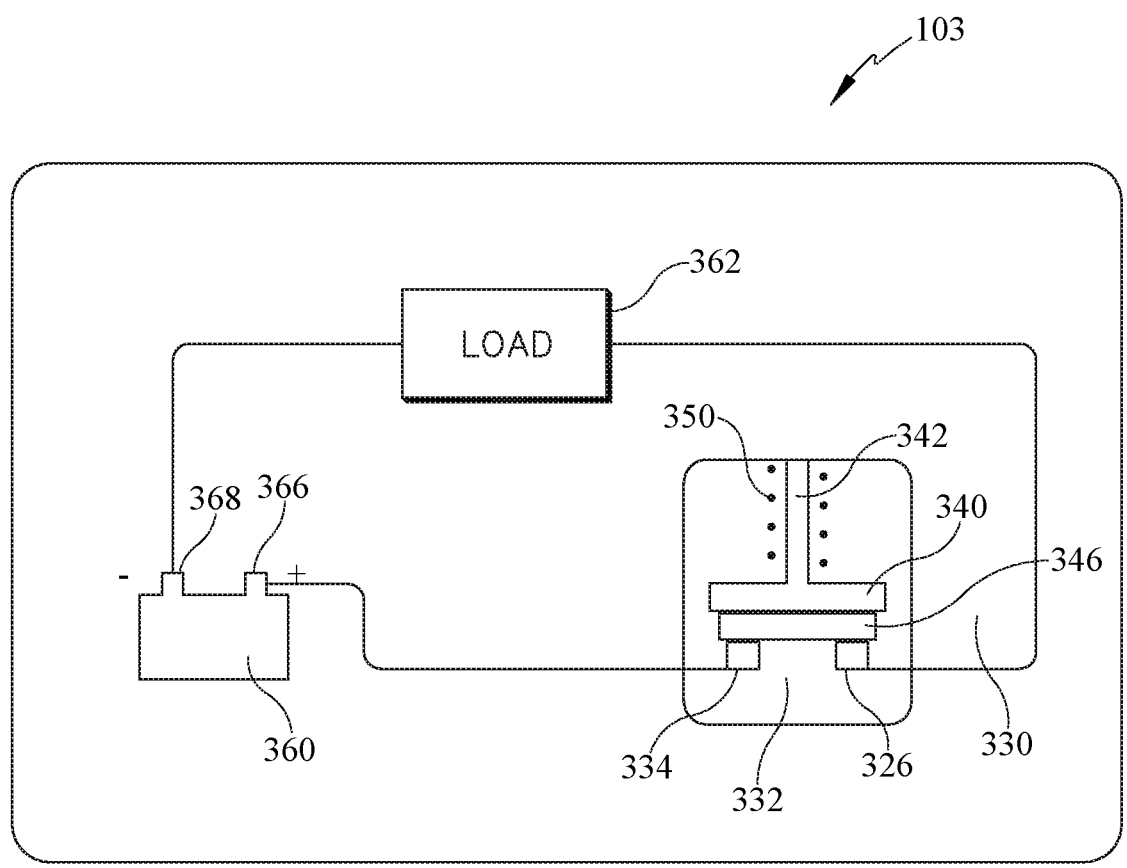
FIG. 35
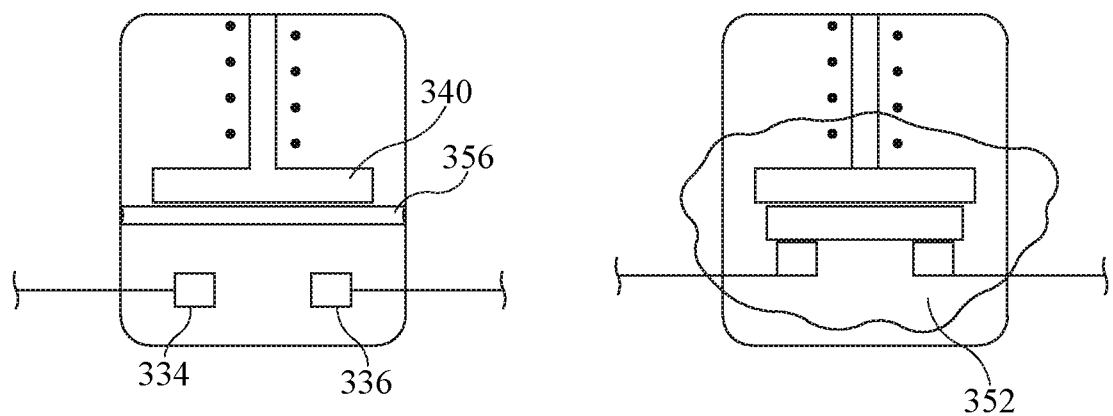
FIG. 37
FIG. 36

INCONTINENCE DETECTION APPARATUS HAVING DISPLACEMENT ALERT

CROSS-REFERENCE TO RELATED APPLICATION

This application is a continuation of U.S. application Ser. No. 14/186,522, filed Feb. 21, 2014, which claims the benefit of and priority to U.S. Provisional Application Ser. No. 61/778,830, filed Mar. 13, 2013, each of which is hereby incorporated herein by this reference.

SUMMARY

The subject matter described herein relates to methods and apparatuses for the detection of incontinence or other moisture, and to methods of analysis of detected fluids and to multifunctional sensor systems. The present invention may comprise one or more of the features recited in the appended claims and/or one or more of the following features or combinations thereof.

One embodiment of a method of interrogating a sensor to detect the presence of moisture on an occupant support comprises the steps of A) providing a moisture responsive sensor in a surveillance zone of the occupant support, the sensor being tuned to a center frequency; B) exciting the sensor with an electromagnetic signal having a frequency approximately equal to the center frequency; C) monitoring for a center frequency response from the sensor; D) comparing the center frequency response to an expected center frequency response; and E) if the center frequency response compares favorably to an expected center frequency response, issuing a first output consistent with the favorable comparison.

BRIEF DESCRIPTION OF THE DRAWINGS

The foregoing and other features of the various embodiments of the methods and apparatuses described herein will become more apparent from the following detailed description and the accompanying drawings in which:

FIG. 11 shows a sample correlation useful in the method of FIG. 10.

FIGS. 35-36 show a system including a sensor pad which may be an incontinence pad, and which includes a switch and a fuse in the form of a patch of material and in which the switch has an open state in which the fuse impedes the establishment of an electrical connection between switch terminals and a closed state in which the fuse enables the establishment of the electrical connection in response to a stimulus having acted on the fuse.

FIG. 37 shows an alternative embodiment of FIGS. 35-36 in which the fuse is a membrane.

DETAILED DESCRIPTION

System for Detecting Incontinence or Other Moisture Caused Abnormality.

Figure 1A:
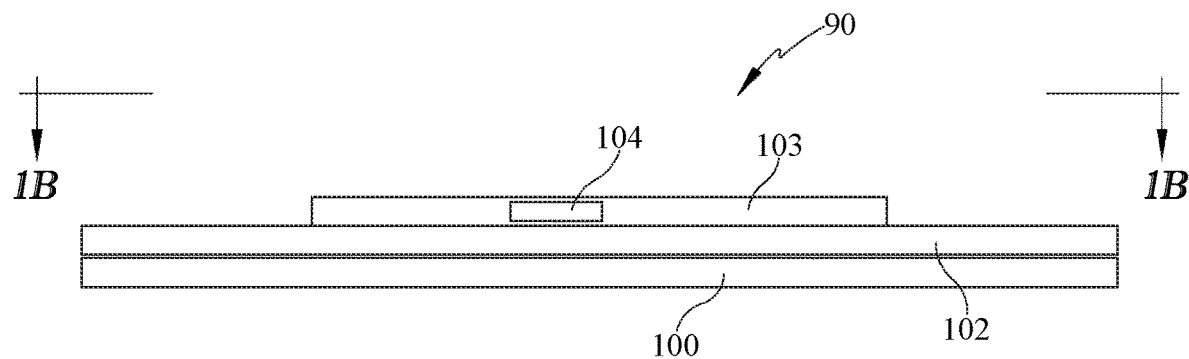
FIGS. 1A and 1B are schematic side elevation and plan views of an occupant support exemplified as a bed such as a hospital bed and showing a sensor mat resting on a mattress of the bed and also showing associated components of a system for detecting moisture on the occupant support.
Figure 1B:
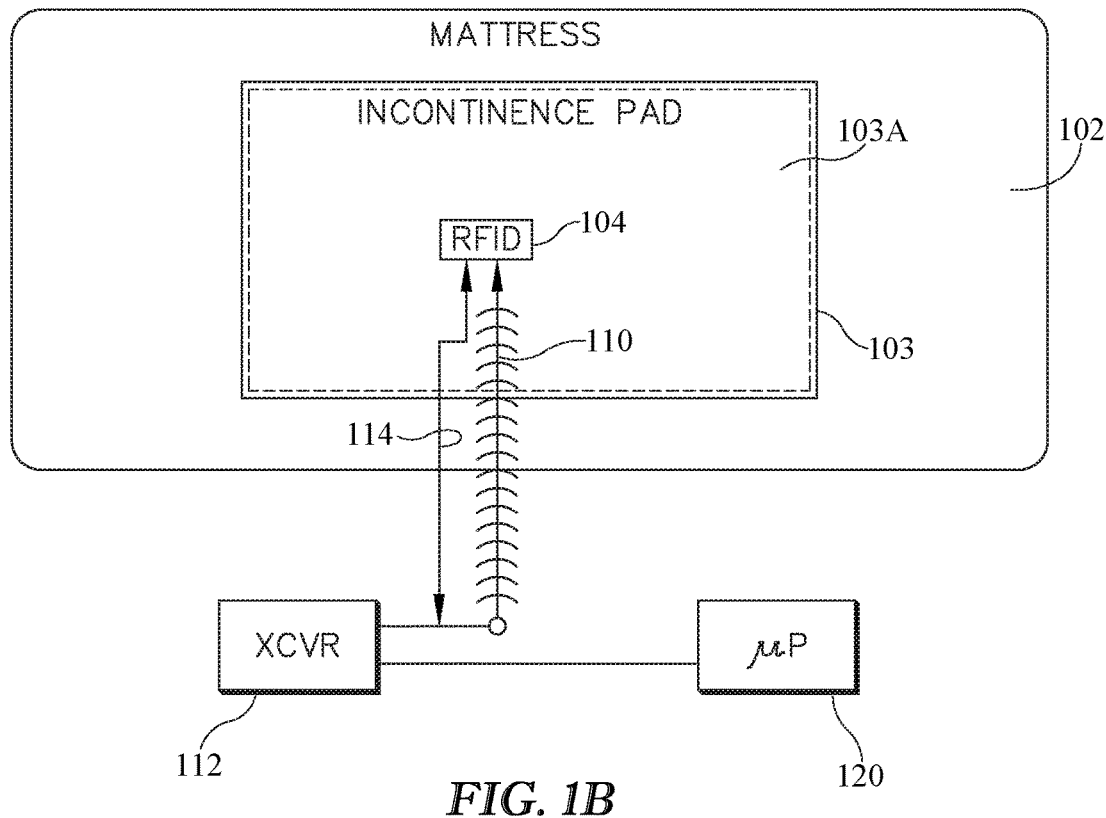

FIGS. 1A-1B schematically show an occupant support 90 such as a hospital bed 90. The bed includes a frame 100, and a mattress 102 supported on the frame. An incontinence pad 103 rests on the mattress in an area or zone 103A (dashed lines) thereof in which it is desired to conduct surveillance for unwanted moisture or other moisture related abnormality. In the illustrated occupant support the surveillance zone is substantially congruent with the pad 103. Although the pad is referred to as an incontinence pad and this application uses incontinence accidents (urine) as an example, the moisture of concern may be other forms of moisture such as perspiration, blood, water, perspiration, or moisture present in material such as fecal matter which has moisture content.

Figure 3:
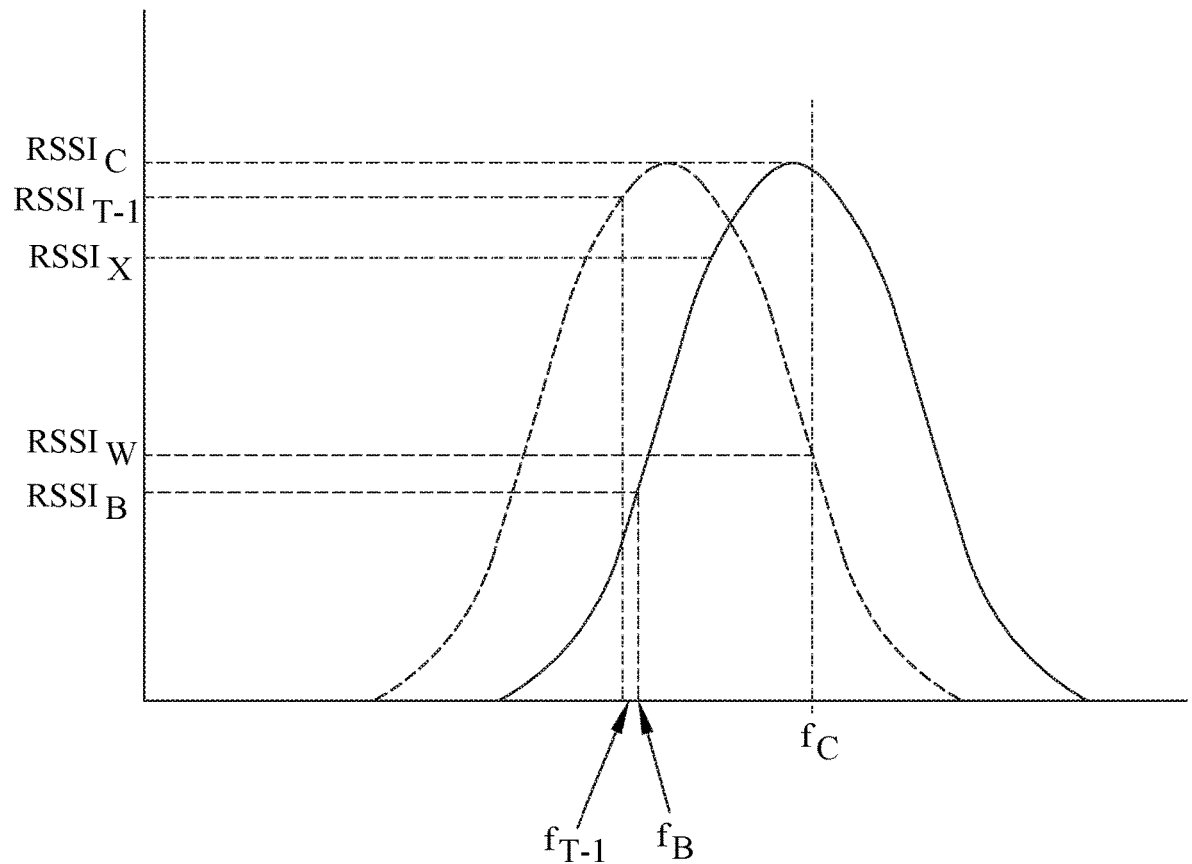
FIG. 3 is a graph showing the Return Signal Strength Indicator (RSSI) of an RFID sensor in a baseline state (solid line) and in a mistuned state (dashed line), which mistuned state may be attributable to the presence of moisture on the RFID.

The system for detecting the presence of moisture on the occupant support includes moisture responsive sensor 104, which is part of the pad. The example sensor described in the examples of this application is an RFID (Radio Frequency Identification) tag or sensor tuned to a center frequency. This is seen in FIG. 3 where the solid line bell shaped curve represents the tuning of the RFID sensor and the center frequency is labeled fC. When the RFID is excited by an electromagnetic signal 110 having a frequency at or near fC, for example a signal generated by a transceiver 112 such as Texas Instruments model TRF7960 transceiver, the RFID returns a return or response signal 114 whose Return Signal Strength Indicator (RSSI) in the transceiver is strong. For example, considering the solid line bell shaped curve of FIG. 3, if the transceiver excites the RFID at fC it receives a response whose RSSI is RSSIC. If the transceiver excites the RFID at fB (which is not near the tuned frequency), the transceiver receives a response whose RSSI is RSSIB. Whether the RSSI of the return signal is considered to be "strong" or "weak" for a given application of the RFID is determined by a designer of the given application.

The transceiver 112 is adapted to excite the sensor 104 with an electromagnetic signal 110 having a frequency approximately equal to the center frequency of the sensor and to monitor for a center frequency response from the sensor. "Center frequency response" means the RSSI of the return signal returned as a result of the sensor having been excited at its center frequency.

The system for detecting the presence of moisture on the occupant support also includes a processor 120 adapted to compare the center frequency response to an expected center frequency response. For example the expected center frequency response for the center frequency fC of FIG. 3 (continuing to refer to the solid line bell shaped curve) is RSSIC plus or minus some tolerance, e.g. between RSSIC and RSSIX. The processor also issues an output, referred to as a first output, if the center frequency response compares favorably to an expected center frequency response, e.g. if the RSSI is between RSSIC and RSSIX. The comparison is considered to be a favorable one (and the RSSI is considered to be strong) if the RSSI is within the expected range or tolerance, for example between RSSIC and RSSIX.

If the center frequency response does not compare favorably with the expected center frequency response (e.g. if the return signal RSSI is a weak response such as RSSIW) this may be the result of the tuning of the RFID sensor having changed, for example due to contamination of the RFID antenna by moisture. This is indicated by the dashed line bell shaped curve. Therefore, the processor commands the transceiver to excite the sensor with one or more electromagnetic test signals having test frequencies different than the center frequency for example fT1, which exceeds fC by a specified delta frequency, fT2 which exceeds fT1 by a delta frequency, fT-1 which is smaller than fC by a delta frequency, fT-2 which is lower than fT-1 by a delta frequency, and so forth. The above mentioned delta frequencies may be equal or unequal. The processor compares the test frequency response (the response the transceiver receives as a result of having excited the RFID at the test frequency) to an expected or desired test frequency response corresponding to the test frequency. If the test frequency response from the sensor compares favorably to an expected or desired test frequency response which corresponds to the test frequency, the processor issues a second output consistent with the favorable comparison between the test frequency response and the expected test frequency response corresponding to the test frequency. In the example of FIG. 3 the excitation at frequency fT-1 yields a return or response signal whose RSSI at the transceiver is a strong signal whose RSSI is $RSSI_{T-1}$ which is approximately equal to the return expected in response to excitation at center frequency fC. The fact that the response to fC is a weak response (RSSIB) and that the response at fT-1 is strong, reveals that the tuning of the sensor has changed, for example because of the RFID antenna having been contaminated with moisture. This is indicated by the position of the dashed line bell shaped curve relative to that of the solid line bell shaped curve.

The expected or desired test frequency response may be the RSSI associated with an "in-tune" RFID (plus or minus a tolerance) or may be an RSSI expected of an RFID tuned to the test frequency and which is not necessarily the same as the RSSI of the in-tune RFID.

The above described excitation at various test frequencies may be discontinued as soon as an excitation at one of those frequencies returns a response that compares favorably with the expected or desired response. Alternatively, the excitation may be carried out at several or all of a set of test frequencies irrespective of the comparative results, and the responses may all be analyzed to determine whether or not the second output should be issued.

If the test frequency response from the sensor does not compare favorably to an expected test frequency response corresponding to the test frequency at any of the test frequencies, the processor issues a third output consistent with the unfavorable comparisons between the test frequency responses and the expected test frequency response corresponding to each of the test frequencies.

In the foregoing example and many others in this application the sensor is an RFID sensor and therefore the electromagnetic excitation signals are radio frequency signals.

RSSI Based Method of Sensor Interrogation for Detecting Incontinence or Other Moisture Caused Abnormality.

Figure 2:
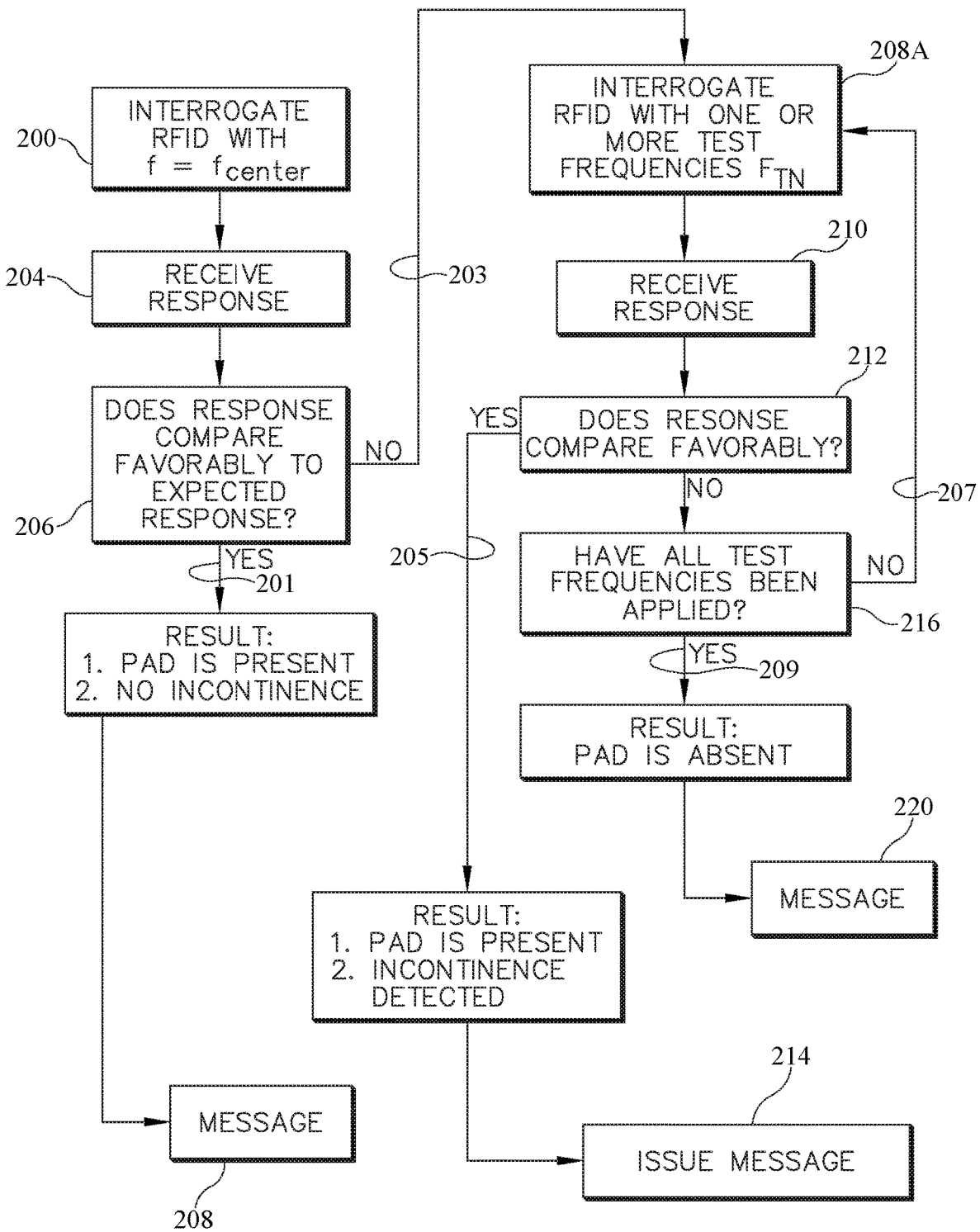
FIG. 2 is a block diagram of a method for interrogating a sensor to detect the presence of moisture on an occupant support.

The block diagram of FIG. 2 shows a method of interrogating a sensor to detect the presence of moisture on an occupant support. The method may be used with the architecture of FIGS. 1A and 1B. A moisture responsive sensor 104 is provided in the in a surveillance zone 103A of the occupant support. The sensor is tuned to a center frequency fC (FIG. 3). At block 200 the sensor is excited with an electromagnetic signal 110 having a frequency approximately equal to the center frequency. At block 204 transceiver 112 monitors for and receives a center frequency response from the sensor. The response may be a strong response or a weak response. The response may also be a "null" response, i.e. a response of no discernible RSSI or other indication of strength. At block 206 microprocessor 120 compares the center frequency response to an expected or desired center frequency response. If the center frequency response at block 206 compares favorably to the expected or desired center frequency response, the method follows path 201 so that the processor issues a first output 208 consistent with the favorable comparison. As seen in the illustration the first output is an indication that an incontinence pad is present and no incontinence is detected.

If the center frequency response does not compare favorably with the expected center frequency response, the method follows path 203. At block 208A the processor causes the transceiver to excite the sensor with one or more electromagnetic test signals having test frequencies different than the center frequency. After each excitation the transceiver monitors for a test frequency response at block 210. At block 212 the processor determines if the test frequency response from the sensor compares favorably to an expected test frequency response corresponding to the test frequency. If so, the method follows path 205 and processor 120 issues a second output 214 consistent with the favorable comparison between the test frequency response and the expected or desired test frequency response corresponding to the test frequency. The second output 214 is an indication that an incontinence pad is present and that incontinence has been detected. If not, the method proceeds to block 216 where the processor determines if all test frequencies of interest have been applied. If not, the method follows path 207 and applies additional test frequencies (block 208) and continues to monitor for a return (block 210) that compares favorably (block 212). If all test frequencies have been applied (block 216) without having received a favorable response (block 212) the method follows path 209 and the processor issues a third output consistent with the unfavorable comparison between the all the test frequency responses and their corresponding expected test frequency response. The third output is an indication that an incontinence pad is absent or a fault has occurred. The conclusion that the pad is absent may mean that the pad has been removed from the mattress, or it may mean that is has been displaced along the mattress far enough that it is out of communication with the transceiver.

As noted above in the context of the architecture of FIGS. 1A and 1B, the second output may be issued in response to a favorable comparison and without first exciting the sensor at any other test frequencies. Alternatively issuance of the second output may be deferred until at least one additional test frequency has been applied to the sensor or until all test frequencies of interest have been applied to the sensor, even if an earlier applied frequency yields a favorable comparison between the test frequency response and the expected or desired response at that test frequency. That is, the second output is not issued until the sensor has been excited at at least one frequency other than the test frequency that yielded a favorable comparison.

Rate of Change Based Method of Sensor Interrogation for Detecting Incontinence or Other Moisture Caused Abnormality.

Figure 4:
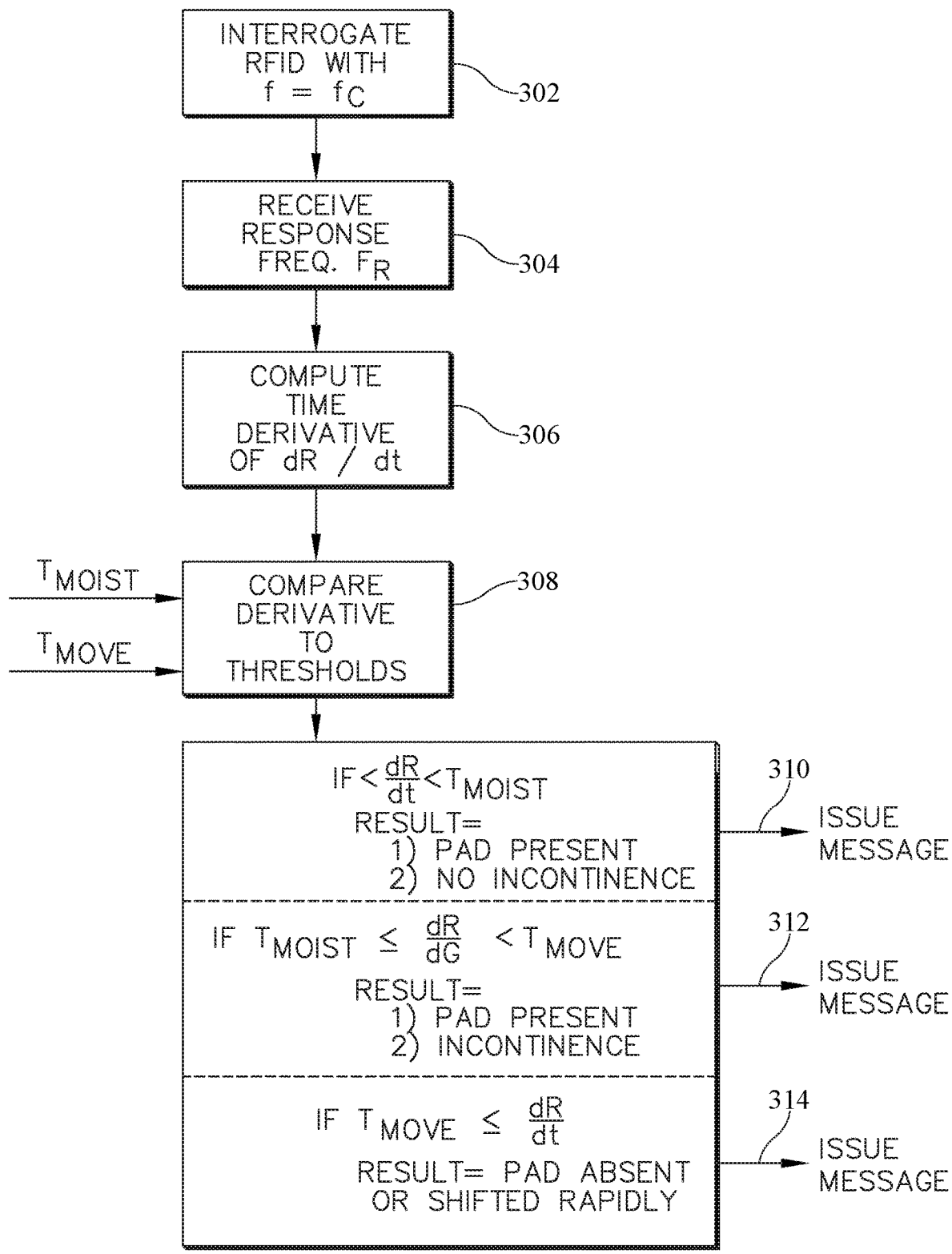
FIG. 4 is a block diagram showing another method of interrogating a sensor to detect the presence of moisture on an occupant support.

FIG. 4 shows a related method of interrogating a sensor to detect the presence of moisture on an occupant support. The method may be used with the architecture of FIGS. 1A and 1B. As with the method of FIG. 3 the method includes providing a moisture responsive sensor 104 in a surveillance zone 103A of the occupant support. The sensor is tuned to a center frequency. The method also includes exciting the sensor with an electromagnetic signal having a frequency approximately equal to the center frequency (block 302) as in FIG. 2 and monitoring for and receiving a center frequency response from the sensor (which response may be a null response) (block 304).

The method recognizes that the tuning of the sensor will change as a function of moisture and that the rate at which the tuning changes can indicate the presence or absence of moisture.

Figure 5:
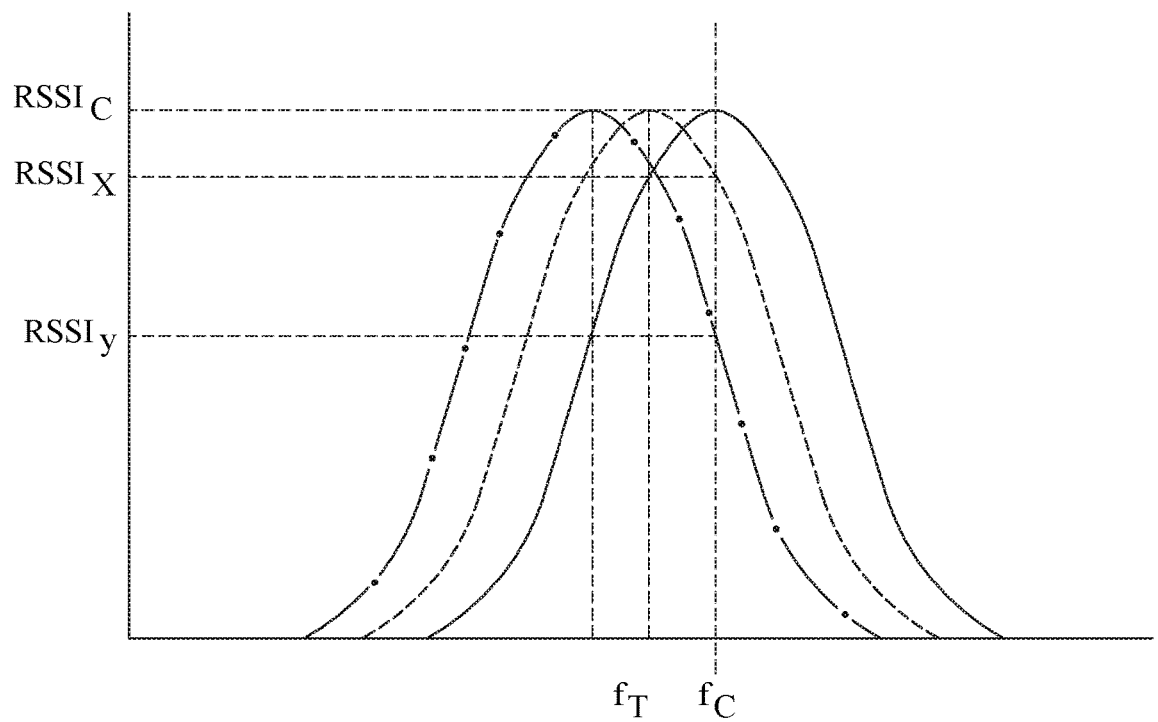
FIGS. 5-7 are illustrations showing two possible ways to calculate a derivative useful in the method of FIG. 4.
Figure 6:
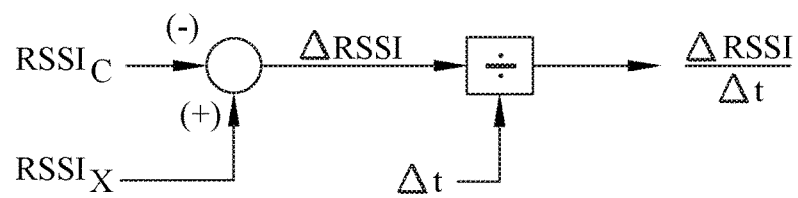
Figure 7:
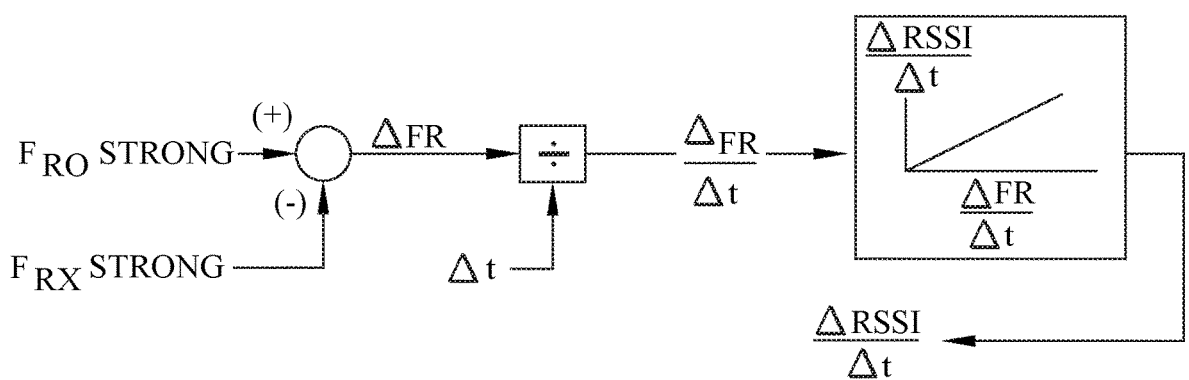

At block 306 the processor calculates a rate of change based on the center frequency responses received at different times. Referring additionally to FIGS. 5-7 two derivative calculations are shown. In FIG. 6 an initial return RSSIC corresponding to an excitation frequency fC is subtracted from a return RSSIX corresponding to an excitation at the same frequency fC applied at a later time. The difference is divided by the time difference delta-t to form a crude derivative dR/dt. The existence of a nonzero derivative (taking measurement tolerances and calculation induced inaccuracies into account) may be the result of the sensors becoming progressively out of tune (i.e. shifting from the solid bell curve to the dashed curve to the dash dot curve of FIG. 5), which yields RSSI's of RSSIC, RSSIX and RSSIY at three different times. FIG. 7 shows an alternate derivative calculation. In the alternate calculation the sensor is interrogated at fC. If the return received by the transceiver 112 changes from strong at one time t0 to weaker at a later time tX, one or more test frequencies not equal to fC are applied at time tX (the time required to apply the one or more additional test frequencies is negligible) until a strong return is again received. The processor uses the information about which excitation frequencies FR0, FRX yielded strong responses, and the time between receiving the strong returns to calculate the derivative dR/dt.

In the method of FIGS. 5-6, the calculated rate of change is a function of a change in RSSI over an interval of time. In the method of FIG. 7 the calculated rate of change is a function of the difference between two excitation frequencies each of which produces a response having approximately equal RSSI values and a correlation describing a relationship between the frequency change and the presence or absence of moisture. Other correlations may enable a determination of the identity or properties of the fluid, e.g. blood, perspiration, acidic fluid, alkaline fluid, and so forth.

Returning now to FIG. 4, the method proceeds to block 308 and compares the calculated derivative to one or more thresholds. In the example shown the derivative is compared to two thresholds Tmoist and Tmove. The processor 120 issues an output in response to the comparison as set forth in Table 1 below, in which the rate of change is denoted as dR/dt:

TABLE 1

| Condition | Issued Output |
| --- | --- |
| dR/dt < TMOIST | First (310) |
| TMOIST ≤ dR/dt < TMOVE | Second (312) |
| TMOVE ≤ dR/dt | Third (314) |

In the context of detecting incontinence, the first output 310 is an indication that an incontinence pad is present and no incontinence is detected, the second output 312 is an indication that an incontinence pad is present and incontinence has been detected, and the third output 314 is an indication that an incontinence pad is absent.

System for Detecting Incontinence or Other Moisture Caused Abnormality Based on Protected and Exposed Sensors.

Figure 8:
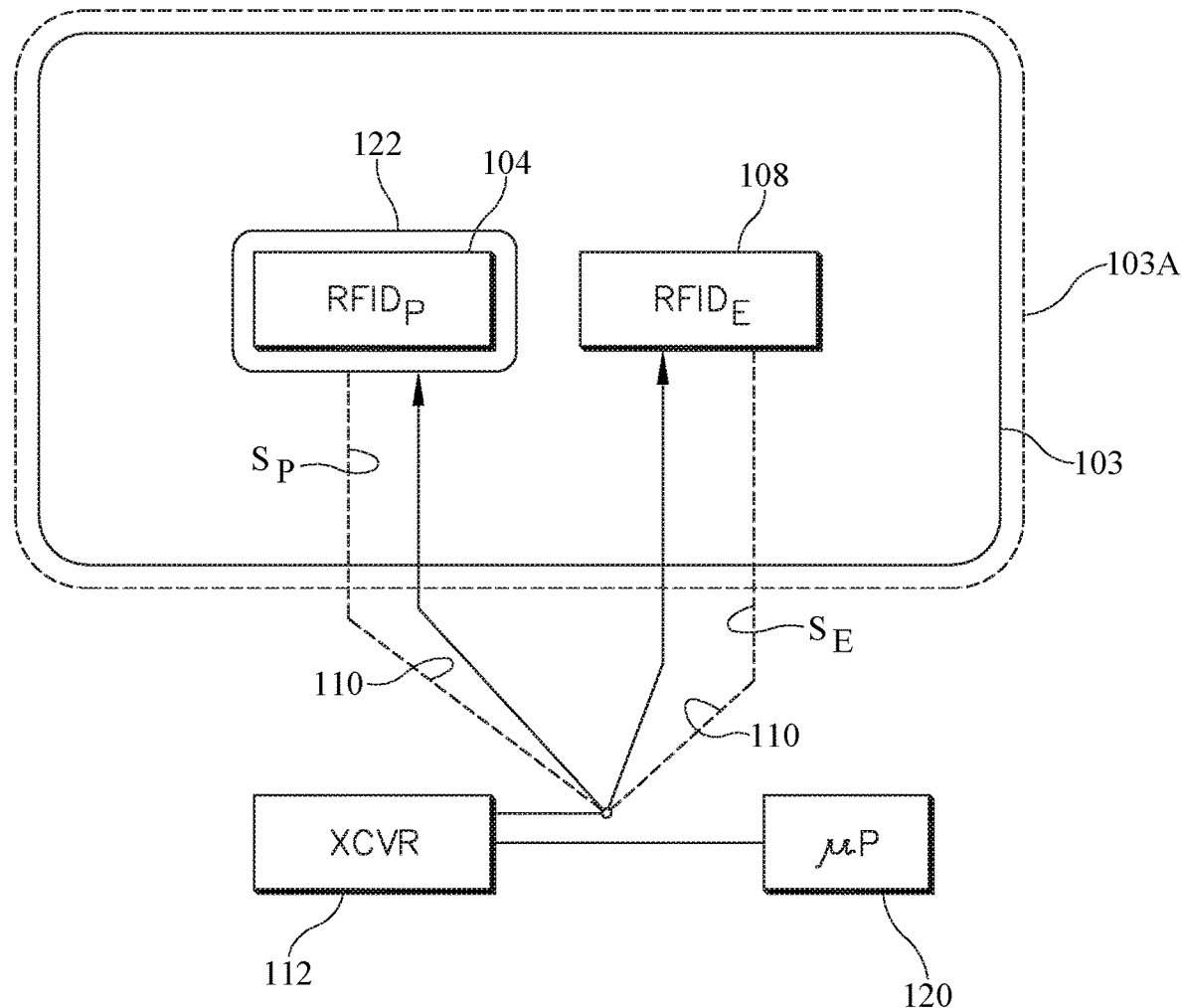
FIG. 8 is a schematic view of a system for detecting the presence of moisture on an occupant support.

FIG. 8 shows a system for detecting the presence of moisture on an occupant support. The system comprises an incontinence pad 103, a transceiver 112 and a microprocessor 120. The pad includes first and second moisture responsive sensors for example RFID's 104, 108 (also labelled RFIDP and RFIDE) in a surveillance zone 103A of an occupant support. Each sensor is tuned to a center frequency. The sensors may be tuned to approximately the same center frequency or to different center frequencies. Sensor RFIDP is enclosed in a moisture proof or moisture resistant enclosure 122 and therefore is also referred to as a protected sensor. Sensor RFIDE is not protected from moisture which may be present on the pad in the surveillance zone and therefore is referred to as an exposed sensor.

Transceiver 112 is adapted to excite each sensor RFIDP, RFIDE with an electromagnetic signal having a frequency approximately equal to its center frequency and to monitor for a center frequency response from each sensor;

Processor 120 is adapted to compare the center frequency response SP of the first (protected) sensor to an expected center frequency response of the first sensor and to compare the center frequency response of the second sensor SE to an expected center frequency response of the second sensor, or equivalently to assess the response as "strong" or as "weak or absent". The processor is further adapted to issue an output as set forth in Table 2 below:

TABLE 2

| Result of comparison (response vs expected response) or assessment for first (protected) sensor | Result of comparison (response vs expected response) or assessment for second (exposed) sensor | Output |
| --- | --- | --- |
| RSSI strong | RSSI strong | no moisture detected |
| RSSI strong | RSSI weak or absent | moisture detected |
| RSSI weak or absent | RSSI strong | fault |
| RSSI weak or absent | RSSI weak or absent | sensor not present or sensor moved or fault |

If the response from both sensors is strong, the sensors, and therefore pad 103, are present but the system is not detecting moisture. Accordingly the output ("no moisture detected") is consistent with that finding. If the response from the protected sensor is strong and the response from the exposed sensor is weak or absent, the mat is present (as revealed by the strong signal from the protected sensor, which, because of enclosure 122, has not suffered any change of tuning as a result of the presence of moisture) and moisture is also present (as revealed by the weak signal from the exposed sensor which has become mistuned as a result of the presence of moisture). Accordingly the output is consistent with that finding ("moisture detected"). If the response from the protected sensor is weak or absent and the response from the exposed sensor is strong it is likely that a fault exists. Accordingly the output is consistent with that finding ("fault"). If the response from both sensors is weak or absent there may be a fault or the mat may have been removed from the occupant support mattress or the position of the pad on the mattress may have changed enough that the sensors are out of range of the transceiver.

Method of Sensor Interrogation for Detecting Incontinence or Other Moisture Caused Abnormality Based on Protected and Exposed Sensors.

Figure 9:
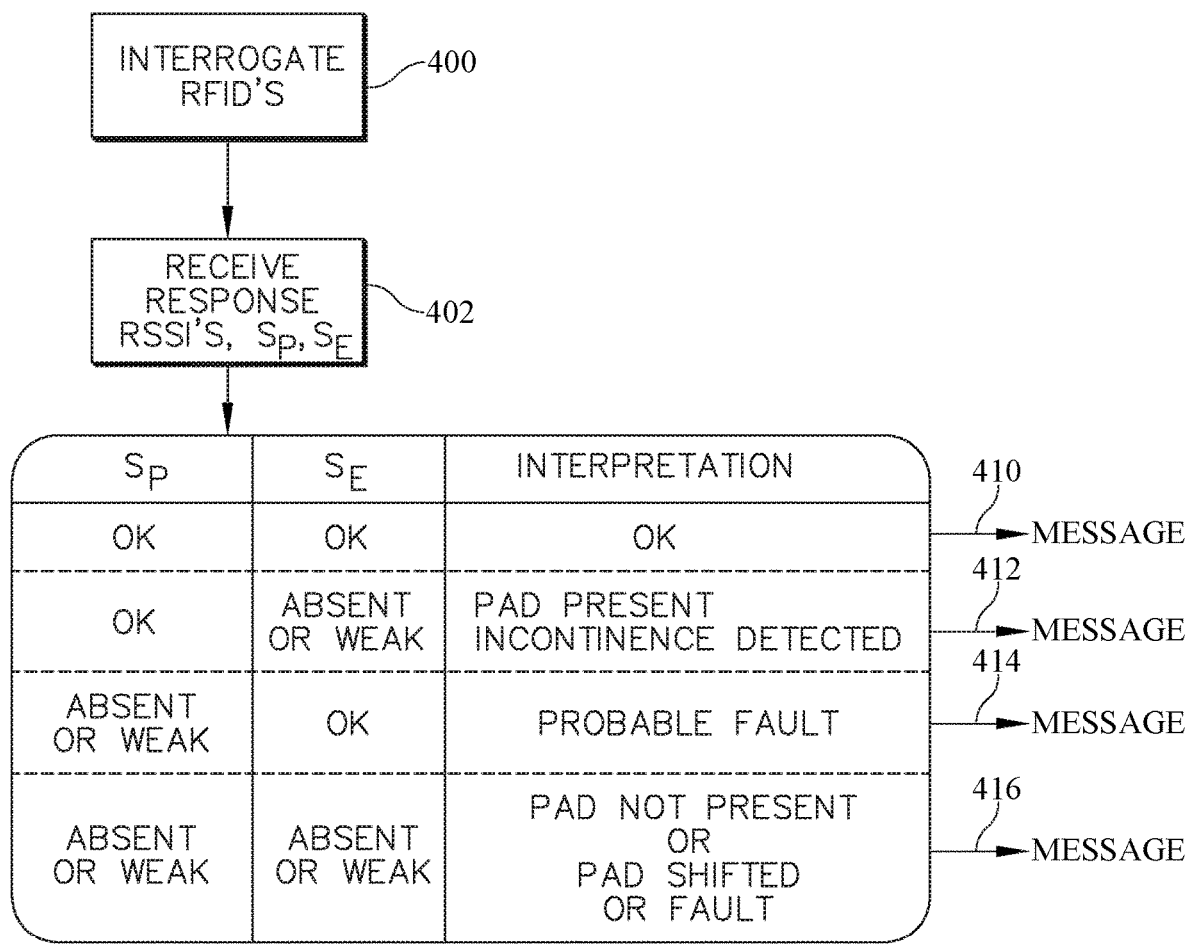
FIG. 9 is a block diagram showing another method of interrogating a sensor suite to detect the presence of moisture on an occupant support.

FIG. 9 is a block diagram showing a method of interrogating a sensor suite (which may be a suite of two sensors as in FIG. 8) to detect the presence of moisture on an occupant support. The method may be used with the architecture of FIG. 8. Referring to FIGS. 8 and 9 the method includes providing first and second moisture responsive sensors 104, 108 in a surveillance zone of the occupant support. The sensors are each tuned to a center frequency. First sensor 104 is protected from coming into contact with moisture which may be present in the surveillance zone. Second sensor 108 exposed and therefore is susceptible to coming into contact with moisture which may be present in the surveillance zone.

The method includes exciting each sensor with an electromagnetic signal having a frequency approximately equal to its center frequency (block 400), monitoring for and receiving a center frequency response signal SP from the first, protected sensor, and monitoring for and receiving a center frequency response signal SE from the second, exposed (unprotected) sensor. As with other embodiments the response may be a null response. The method also includes comparing the center frequency responses to an expected center frequency response for each sensor, or equivalently assessing the response from each sensor as "strong" or as "weak or absent".

The method also includes issuing an output 410, 412, 414, or 416) as set forth in Table 3 below:

TABLE 3

| Result of comparison (response vs expected response) or assessment for first (protected) sensor | Result of comparison (response vs expected response) or assessment for second (exposed) sensor | output |
| --- | --- | --- |
| RSSI strong | RSSI strong | no moisture detected |
| RSSI strong | RSSI weak or absent | moisture detected |
| RSSI weak or absent | RSSI strong | fault |
| RSSI weak or absent | RSSI weak or absent | sensor not present or sensor moved or fault |

Method of Fluid Analysis.

Figure 10:
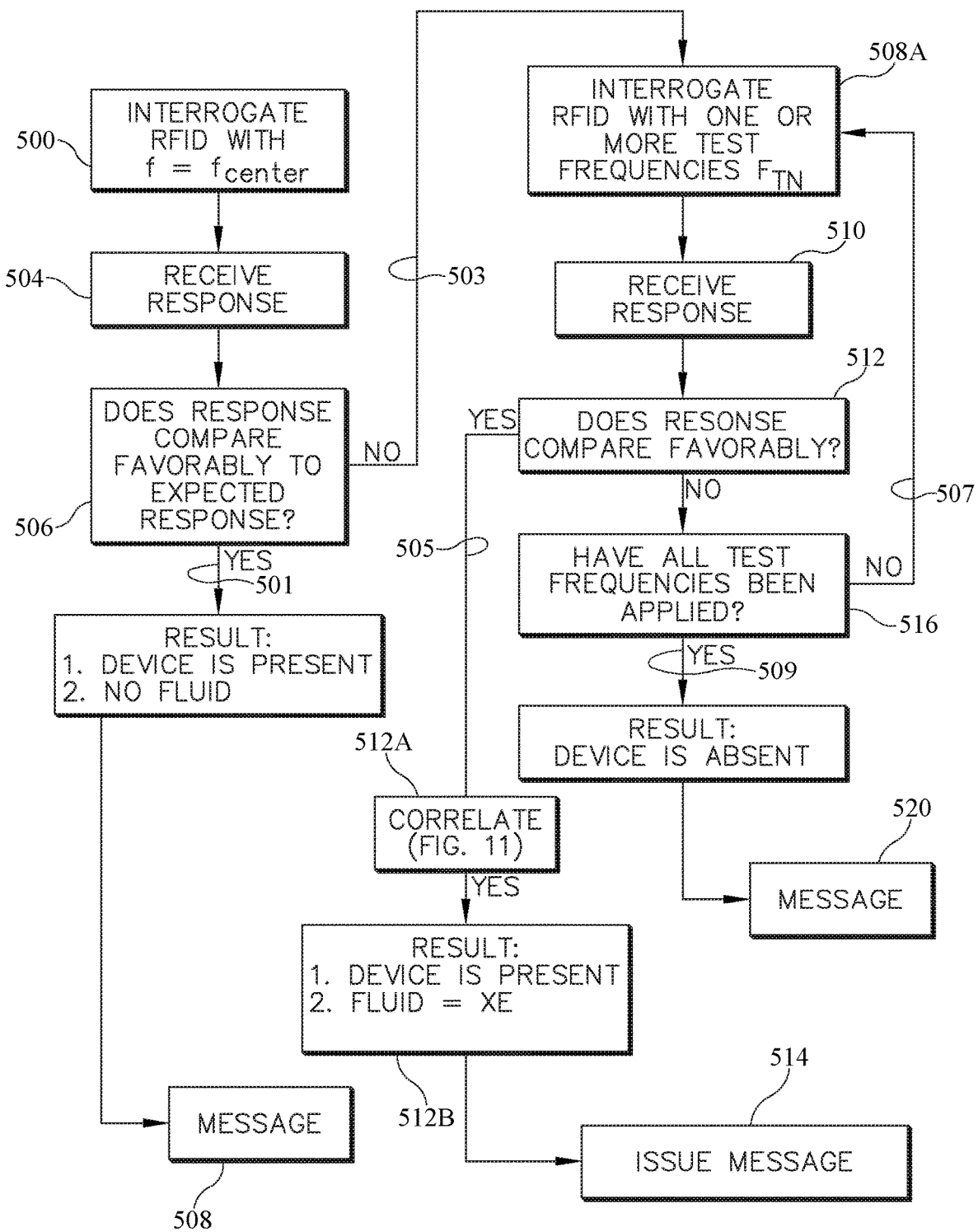
FIG. 10 is a block diagram similar to that of FIG. 2 showing a method of interrogating a sensor to detect the presence of moisture on an occupant support and to analyze moisture which may be present.

FIG. 10 is a block diagram similar to that of FIG. 2 showing a method of interrogating a sensor to detect the presence of moisture on an occupant support and to analyze moisture which may be present. The blocks of FIG. 10 which are analogous to those of FIG. 2 are identified with 500-series reference numerals in lieu of the 200-series reference numerals used on FIG. 2.

The method may be used with the architecture of FIGS. 1A and 1B. A moisture responsive sensor 104 is provided in the surveillance zone 103A of the occupant support. The sensor is tuned to a center frequency fC (FIG. 3). At block 500 the sensor is excited with an electromagnetic signal 110 having a frequency approximately equal to the center frequency. At block 504 transceiver 112 monitors for and receives a center frequency response from the sensor. The response may be a strong response or a weak response. The response may also be a "null" response, i.e. a response of no discernible RSSI or other indication of strength. At block 506 microprocessor 120 compares the center frequency response to an expected or desired center frequency response. If the center frequency response at block 506 compares favorably to the expected or desired center frequency response, the method follows path 501 so that the processor issues a first output 508 consistent with the favorable comparison. As seen in the illustration the first output is an indication that a moisture detecting device is present and no moisture or fluid is detected.

If the center frequency response does not compare favorably with the expected center frequency response at block 506, the method follows path 503. At block 508A the processor causes the transceiver to excite the sensor with one or more electromagnetic test signals having test frequencies different than the center frequency. After each excitation the transceiver monitors for a test frequency response at block 510. At block 512 the processor determines if the test frequency response from the sensor compares favorably to an expected test frequency response corresponding to the test frequency. If not, the method proceeds to block 516 where the processor determines if all test frequencies of interest have been applied. If not, the method follows path 507 and applies additional test frequencies (block 508) and continues to monitor for a return (block 510) that compares favorably (block 512).

Upon detecting a test frequency response that compares favorably to an expected test frequency at block 512, the method proceeds along path 505 to block 512A where the method correlates the test frequency response with a relationship between test frequency response and fluid identity, fluid properties or both. FIG. 11 shows a sample correlation for test frequencies higher than and lower than the center frequency fC. As seen in the illustration the correlation relates a strong RSSI return at a specified frequency to the identity and/or properties of a fluid which, as a result of having contaminated the RFID, retunes the RFID to a frequency other than its noncontaminated center frequency, i.e. to the frequency correlated with the fluid or fluid property. The method then issues a second output 514 consistent with the favorable comparison between the test frequency response and the expected test frequency response and also consistent with the correlation. The second output is an indication that a moisture sensing device is present and that moisture has been detected and is also an indication of the identity of the fluid, the type of fluid or both as defined by the relationship between test frequency response and fluid identity, fluid properties or both.

If, at block 516, the method determines that all test frequencies have been applied (block 516) without having received a favorable response (block 512) the method follows path 509 and the processor issues a third output 520 consistent with the unfavorable comparison between all the test frequency responses and their corresponding expected test frequency response. The third output is an indication that a moisture sensing device is absent or a fault has occurred. The conclusion that the device is absent may mean that it has been removed from the mattress, or it may mean that it has been displaced along the mattress far enough that it is out of communication with the transceiver.

As noted above in the context of the architecture of FIGS. 1A and 1B, the second output may be issued in response to an initial favorable comparison at block 512 and without first exciting the sensor at any other test frequencies. Alternatively issuance of the second output may be deferred until at least one additional test frequency has been applied to the sensor or until all test frequencies of interest have been applied to the sensor, even if an earlier applied frequency yields a favorable comparison between the test frequency response and the expected or desired response at that test frequency. That is, the second output is not issued until the sensor has been excited at at least one frequency other than the test frequency that yielded the initial favorable comparison. This latter method may require a correlation that goes beyond the one dimensional correlation of FIG. 11 in order that processor 120 may properly interpret the significance of multiple strong RSSI returns.

System for Detecting Incontinence or Other Moisture Caused Abnormality Using Multiple RFID's or Other Sensors or Using Multiplexed RFID's or Other Sensors.

Figure 12:
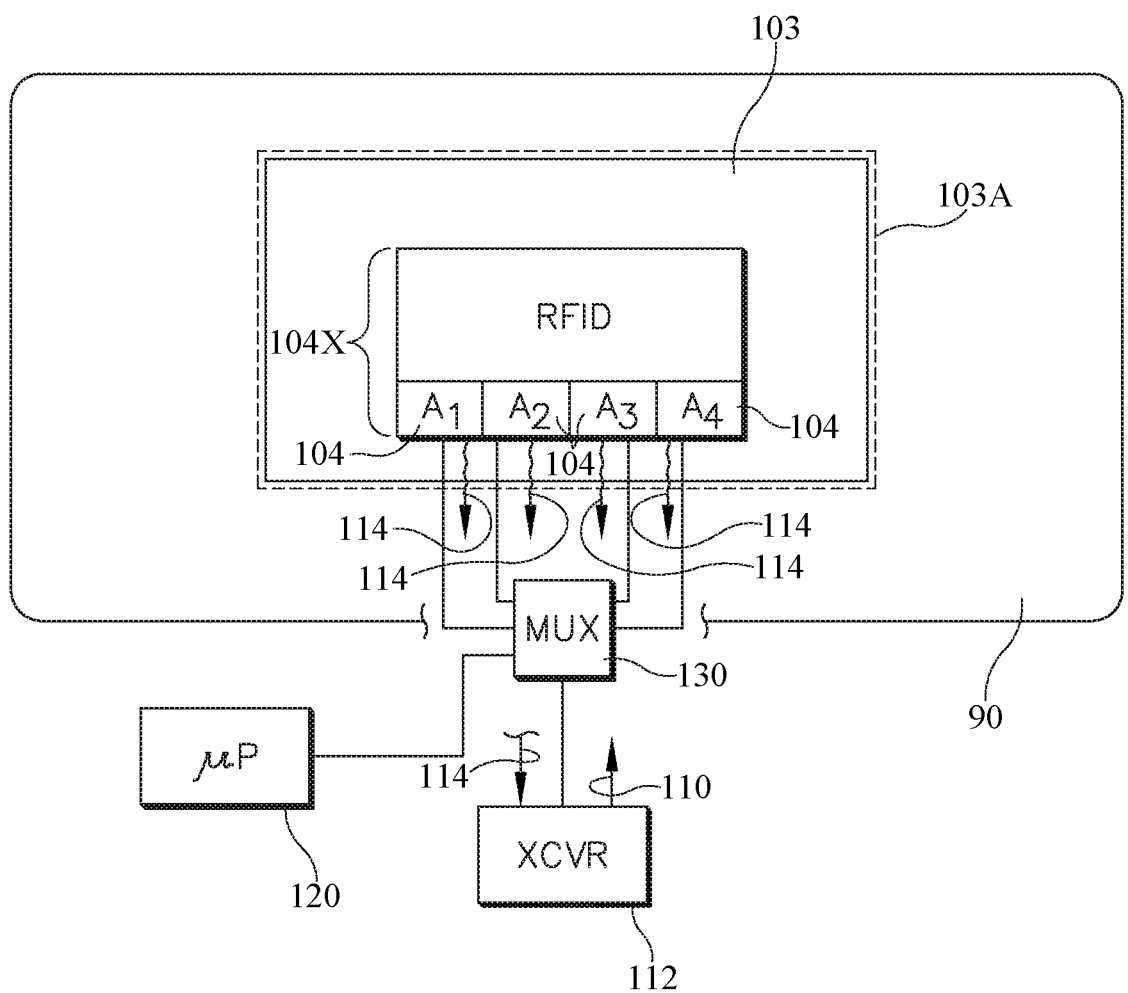
FIG. 12 is a schematic view of a system for detecting the presence of moisture on an occupant support or displacement of a sensor or both.

FIG. 12 shows a system for detecting the presence of moisture on an occupant support or displacement of a sensor or both.

The system includes multiple moisture responsive sensors 104 spatially distributed in a surveillance 103A zone of an occupant support 90. In the illustrated embodiment sensors 104 are individual antenna components (A1, A2, A3, A4) of an RFID sensor assembly 104X. Each sensor is tuned to a center frequency. The system also includes a transceiver 112 adapted to excite the sensors with an electromagnetic signal 110 having a frequency approximately equal to the center frequency and to monitor for a center frequency response 114 from the sensor. The system also includes a multiplexer 130 in communication with each antenna and with the transceiver. The system also includes a processor 120 adapted to command the transceiver to excite the sensors and to analyze the center frequency response of each sensor to detect the presence of moisture on the occupant support or displacement of a sensor or both. The processor 120 is also in communication with the multiplexer so that the processor can govern which of the responses 114 the transceiver detects at any given time. For example the multiplexer may cycle from sensor antenna A1 to sensor antenna A2 to sensor antenna A3 to sensor antenna A4 and then continue repeating the cycle so that the transceiver first detects return signal 114 from A1, then return signal 114 from A2, and so forth.

As already noted sensors 104 are individual antenna components A1, A2, A3, A4 of a sensor assembly 104X. The processor is adapted to command multiplexer 130 to acquire response signals from each antenna component. The illustration shows only a single sensor assembly 104X, however more than one such assembly may be used.

Figure 13:
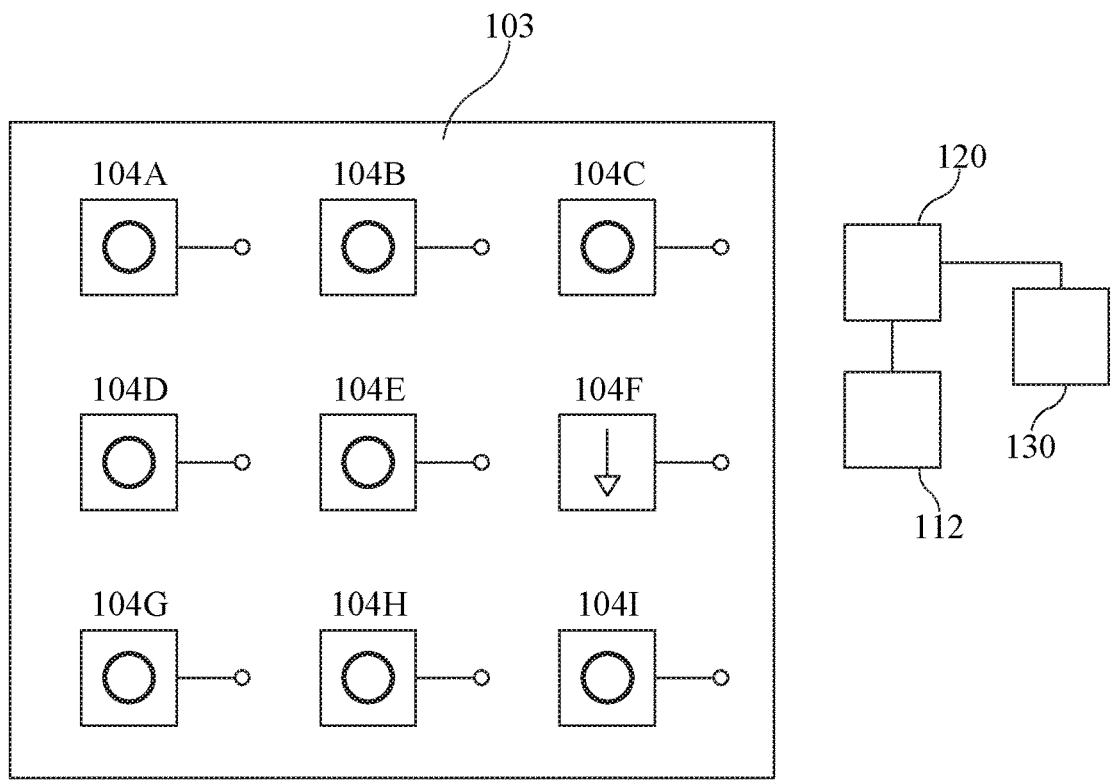
FIGS. 13-14 are schematic plan views each showing a sensor array and an example response to the presence of moisture in contact with at least one of the individual sensors.
Figure 14:
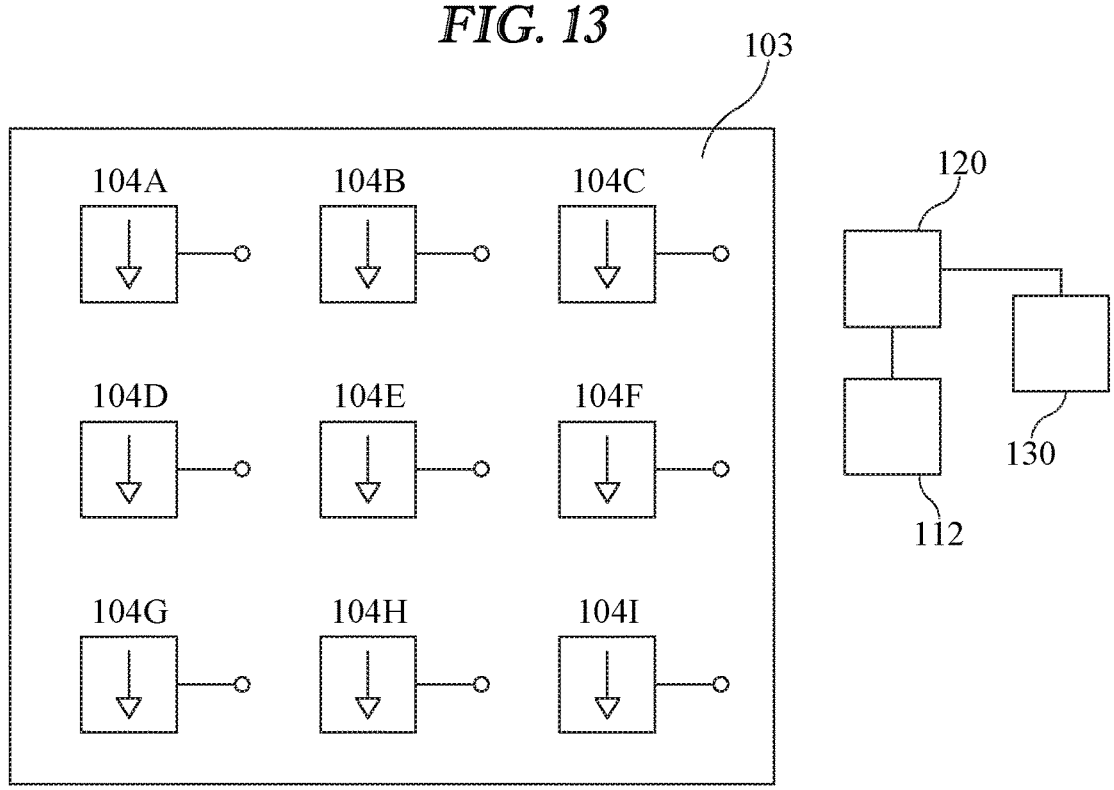

Alternatively the sensors 104 may be individual sensors such as RFID 104 of FIGS. 1A and 1B or RFID's 104A through 104I of FIGS. 13-14, each of which individual sensors has its own antenna A. Processor 130 is adapted to command multiplexer 130 to acquire response signals from each antenna component, e.g. in a successive sequence.

A system may contain one or more assemblies 104X each having two or more antenna components or may have multiple sensors 104 each having its own antenna. Or a system may use a mix of assemblies 104X and individual sensors 104. No matter which option is employed, processor 130 is adapted to command the multiplexer to acquire response signals from all the antennas present whether the antennas are components of a multi-antenna assembly (components 104 of assembly 104X as in FIG. 14) or are dedicated antennas (antennas 104 or A as in FIG. 13).

The processor is also adapted to command the transceiver to analyze the frequency response of each sensor to detect the presence of moisture on the occupant support or displacement of a sensor or both.

Method for Detecting Incontinence or Other Moisture Caused Abnormality Using Multiple RFID's or Other Sensors or Using Multiplexed RFID's or Other Sensors and Based on Highest Return Signal Strength.

Figure 15:
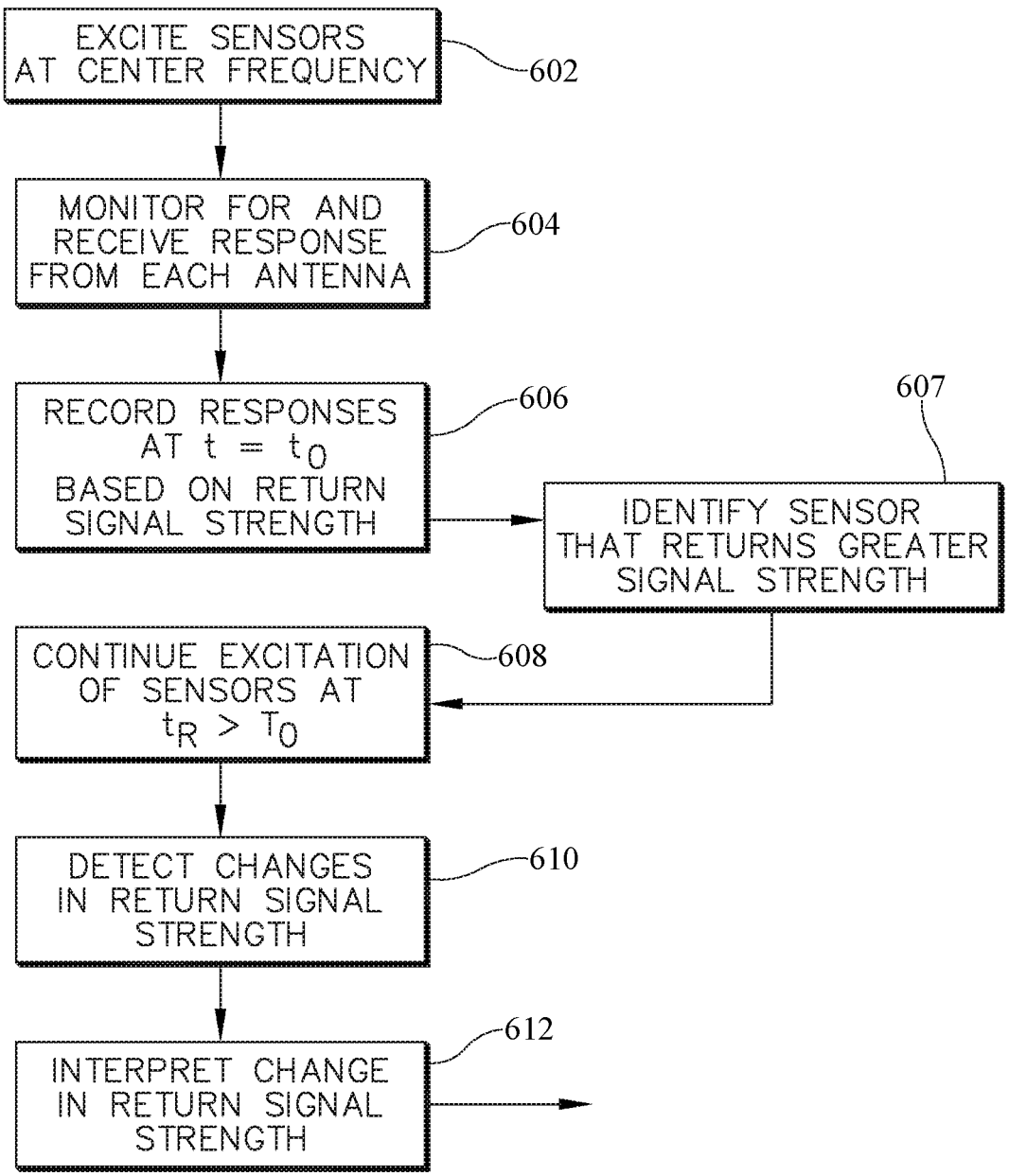
FIG. 15 is a block diagram showing a method of detecting the presence of moisture on an occupant support and of distinguishing between moisture presence and sensor displacement relative to some initial sensor position.

FIG. 15 is a block diagram showing a method of detecting the presence of moisture on an occupant support and of distinguishing between moisture presence and sensor displacement relative to some initial sensor position. The method may be used with the system architecture of FIGS. 12-14.

The method includes providing two or more moisture responsive sensors 104 in a surveillance zone 103A of the occupant support. Each sensor is tuned to a center frequency fC. Transceiver 112 excites the sensors with an electromagnetic signal 110 having a frequency approximately equal to the center frequency (block 602). The transceiver receives center frequency responses from the sensors at a time t0 (block 604). As previously noted the time required for multiplexer 130 to cycle through the sensors is much shorter than any time interval of interest associated with detecting an incontinence event or detecting sensor displacement. Accordingly, any given sampling cycle which occurs between time t−δ and time t+δ is considered to have occurred at time t. The processor identifies which of the sensor returns 114 at time t0 is strongest (block 607). At times t>t0 (blocks 608 and beyond) the transceiver continues to excite at least the identified sensor (and may excite additional sensors as well) (block 608) and receives responses (block 610). The processor carries out an analysis to determine if the return signal strength of the identified sensor has diminished over time. If so the processor analyzes the center frequency return signal strengths from the excitation at time t0 in comparison to the responses obtained as a result of the continuing excitation to detect moisture presence or sensor displacement or both (block 612).

Method for Detecting Incontinence or Other Moisture Caused Abnormality Using Multiple RFID's or Other Sensors or Using Multiplexed RFID's or Other Sensors.

Figure 16:
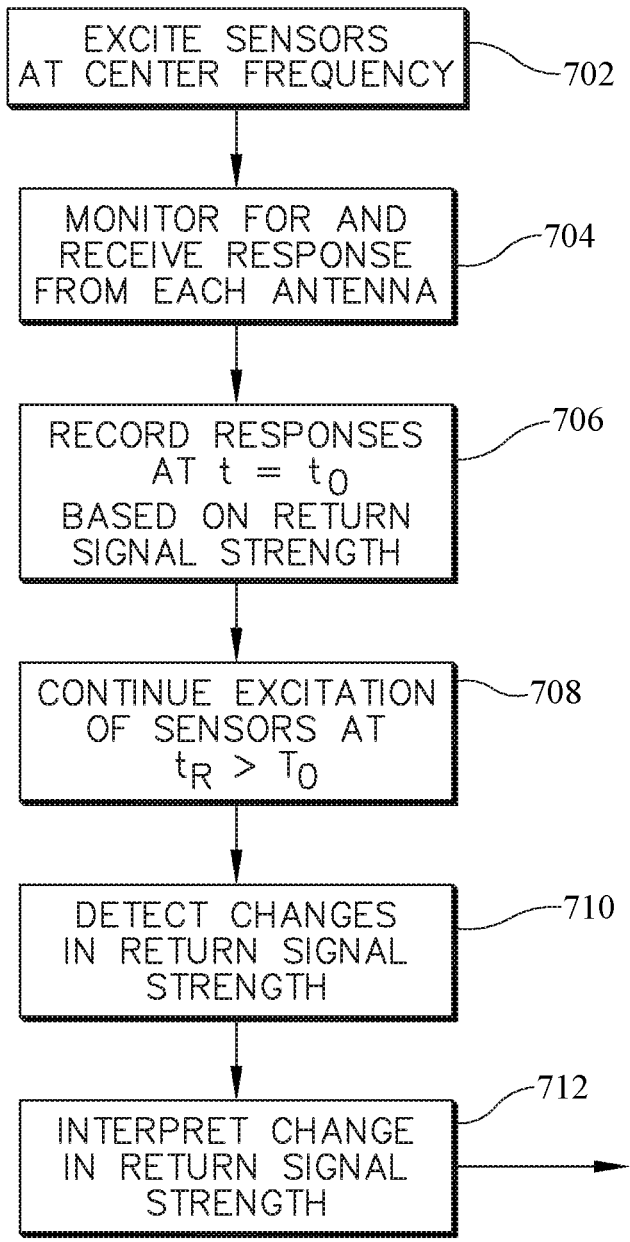
FIG. 16 is a block diagram showing another method of detecting the presence of moisture on an occupant support, displacement of a moisture sensor or both.

FIG. 16 shows another method of detecting the presence of moisture on an occupant support, displacement of a moisture sensor or both. The method includes providing two or more moisture responsive sensors in a surveillance zone of the occupant support, which sensors are tuned to a center frequency. The method may be used with the system architecture of FIGS. 12-14.

Transceiver 112 excites the sensors with an electromagnetic signal 110 having a frequency approximately equal to the center frequency (block 702). Transceiver 112 receives center frequency responses from the sensors (block 704) and records the individual center frequency responses at a time t=0 (block 706). At times t>0 transceiver 112 continues to excite the sensors and to monitor for and receive responses (block 608). At block 710 the processor detects changes in return signal strength, i.e. the differences at times t>0 relative to time t0. At block 712 the processor analyzes the differences determined at block 710 to discern moisture presence, sensor displacement or both.

As noted in the discussion of FIGS. 12-14 the sensors may be individual sensors each having an antenna or may be individual antenna components of a sensor assembly.

FIGS. 13-14 show two examples, both of which rely on a 3×3 array of sensors labeled 104A through 104I. The symbols within each sensor show how that sensor's return frequency response signal (RSSI) has changed between time t0 and a later time. The "0" symbol indicates no change while the downwardly pointing arrow symbols indicate a decrease in return signal strength. In FIG. 13 fewer than all of the sensors exhibit a diminished signal strength (RSSI) and the remainder of the sensors exhibit constant return signal strength. Analysis at block 712 of FIG. 16 therefore reveals that the sensor pad 103 is still in place in it's original (t=t0) position but that the sensors exhibiting reduced strength have been contaminated with moisture. This conclusion is based on the observation that the center frequency response from a first set of one or more sensors (sensor 104F) has become weaker at a time t>0 relative to its center frequency response at an earlier time t0, and that the response of a second set of sensors (all but 104F) which does not include members of the first set (104F) have substantially the same response strength at time t>0 than they did at the earlier time t0.

In FIG. 14 the sensors all exhibit reduced return strength relative to strength at t=0. Hence, the sensors are still in their original location, or have all become moist, or some combination of the two. Distinguishing between the two possibilities or determining that both have occurred can rely on techniques such as those described in the context of FIGS. 2-9. In one embodiment sensor displacement is declared as a result of the center frequency response from all or substantially all the sensors having become weaker at a time t>0 relative to their center frequency response at an earlier time t0.

Hybrid Incontinence Detection System.

Figure 17:
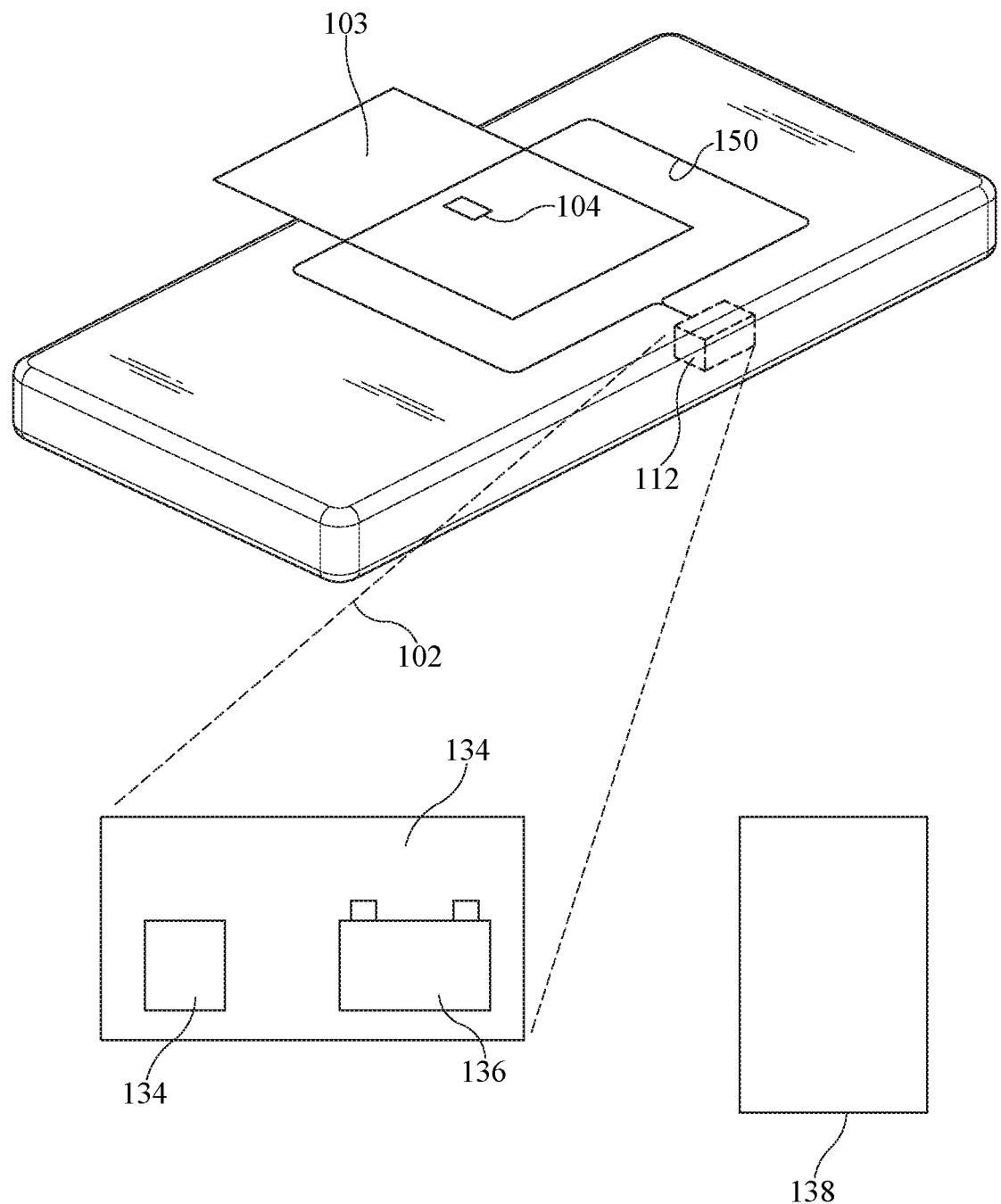
FIG. 17 shows a system in which a transceiver for exciting an RFID tag is integrated into an occupant support.

FIG. 17 shows a system in which the transceiver is integrated into an occupant support. If the occupant support is a bed the transceiver may be integrated into the frame (not shown) or into the mattress 102. The system includes a sensor 104 such as an active or passive RFID tag. Alternatively the sensor may be a circuit printed on a paper. The sensor, irrespective of the technology on which it is based, may be in the form of a sticker. The sensor is made a part of a pad such as incontinence pad 103, for example by sewing or adhering. For example if the sensor is a sticker it may be adhered to the pad. At least the sensor is disposable. The pad may also be disposable.

The system also includes transceiver 112 integrated with the bed, for example with the mattress 102. The transceiver is not considered to be disposable. The system is referred to as a hybrid system because it includes disposable and nondisposable components and because the nondisposable component (the transceiver) is integrated into the occupant support whereas the pad and sensor are easily disassociated from the occupant support.

The sensor is in wireless communication with the reusable transceiver. The transceiver includes a processor chip 134 and may also include a battery 136. In one embodiment the battery is a flexible or foldable battery.

The transceiver is also in wired or wireless communication with a facility information network 138. The communication with network 138 enables an alert to be sent to caregivers to alert them of the incontinence event (or other moisture containing contamination). The communication can also enable updates to be made to electronic records.

In one embodiment a transceiver antenna 150 loops around sensor 104. The antenna may be integral with the mattress or with a ticking or other cover on the mattress. One example of an integral antenna construction is an antenna made of metal thread which is woven or otherwise integrated into the mattress. Another example is a conductive ink applied to the ticking or mattress.

Fluid Reservoir (Absorbent or Dissolving).

FIGS. 18-23 show variants of an architecture for a moisture detection article or pad 103 such as an incontinence pad. The pads include at least one sensor 104 such as an RFID tag. The following discussion of the various embodiments of FIGS. 18-23 relates to the architecture or construction of the pad. The RFID tag or tags can be used for moisture detection and/or analysis as described elsewhere in this specification.

Figure 18:
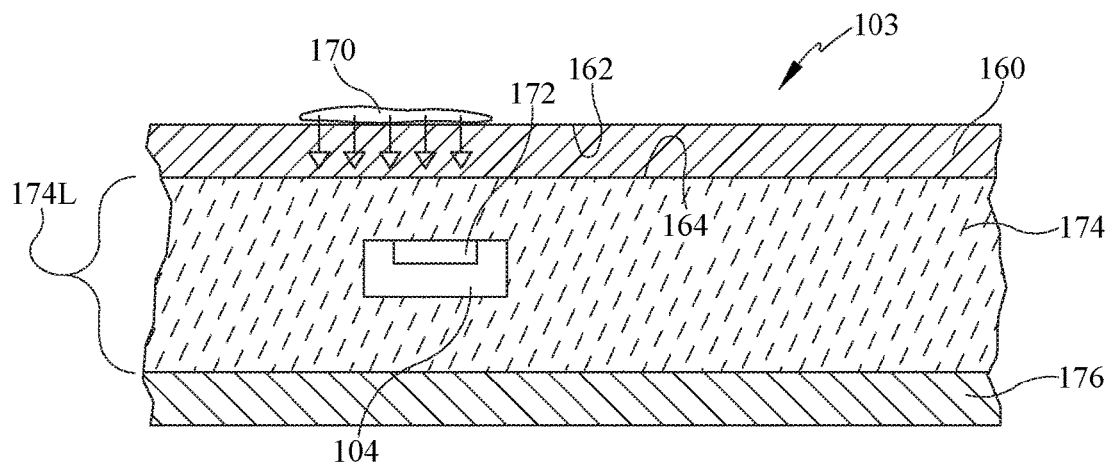
FIGS. 18-23 are schematic side elevation views showing variants of an architecture for a moisture detection article or pad such as an incontinence pad.

Referring first to FIG. 18 the moisture detection apparatus 103 includes a deposition or receptor layer 160 having an exposed side 162 susceptible to moisture contamination and a nonexposed side 164. The deposition or receptor layer is so named because it is the layer of the construction upon which, in customary use, fluid will be deposited or received. The illustration also shows a region or site 170 of actual fluid contamination or deposition.

The apparatus also includes a moisture sensor 104 having a moisture responsive element 172 separated from the deposition layer by a reservoir material 174. The reservoir material is so named because, as will be explained in greater detail below, it introduces an intentional time delay between the initial deposition of fluid on exposed side 162 and contact between the fluid and the moisture responsive element 172. In the embodiments of FIGS. 19-22 the reservoir material is adjacent to the nonexposed side 164 of deposition layer 160 as distinct from being adjacent to the exposed side 162. The apparatus may also include a base layer 176. At least a portion of the base layer is spaced from the deposition layer such that the reservoir material 174 is between the base layer and the deposition layer. Moisture 170 deposited on exposed side 162 must traverse or otherwise overcome the reservoir material in order to come into contact with the moisture responsive element 172. Moisture deposited on exposed side 162 is impeded (by the reservoir layer) from contacting the moisture responsive element 170 until the reservoir layer reacts to the presence of the moisture. As used herein, "reacts" is used in the sense of responding and does not necessarily mean a chemical reaction, but can mean a chemical reaction.

Figure 19:
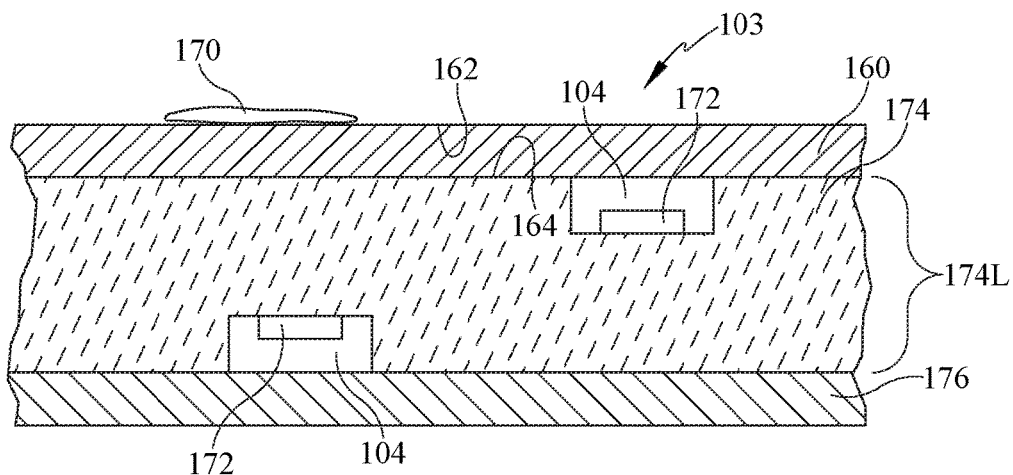

In the variants of FIGS. 18 and 19 the reservoir material is a reservoir layer 174L and the sensor 104 resides within the reservoir layer. The reservoir layer extends between base layer 176 and deposition layer 160. In the variants of FIGS. 18, 20, 21 and 22 the moisture responsive element 172 faces toward the deposition layer. In FIG. 23 the moisture responsive element faces toward the base layer. FIG. 19 shows two sensors, one having a moisture responsive element that faces toward the deposition layer and one having a moisture responsive element that faces toward the base layer. Any particular variant of the architecture may have moisture responsive elements that all face toward the deposition layer or may have moisture responsive elements that all face toward the base layer or may have an assortment of moisture responsive elements some of which face toward the deposition layer and some of which face toward the base layer.

Figure 20:
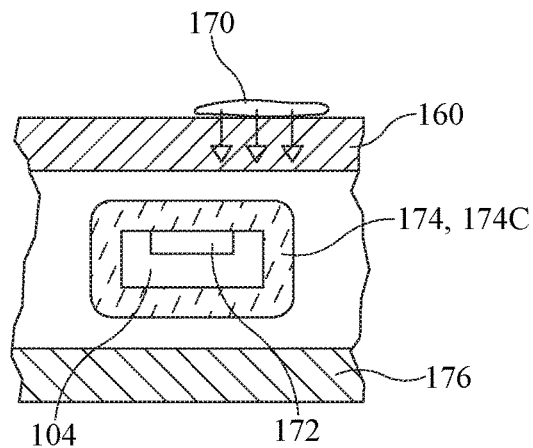
Figure 21:
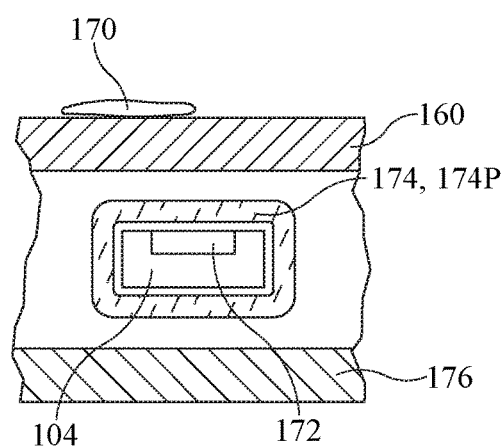

In the variant of FIG. 20 the reservoir material 174 is a coating 174C which encapsulates the sensor 104. In the variant of FIG. 21 the reservoir material 174 is in the form of a pocket 174P which encapsulates the sensor 104. In the embodiments of FIGS. 20-21 (and 23) the reservoir material is considered to be localized whereas in the embodiments of FIGS. 18-19 (and 22) the reservoir material is nonlocalized.

In the embodiments of FIGS. 20 and 23 the reservoir material is a coating over at least the moisture responsive element 172. In FIG. 20 the reservoir material is a coating over the entire sensor 104. In FIG. 23 the reservoir material is a coating that extends only slightly beyond the moisture responsive element.

Figure 22:
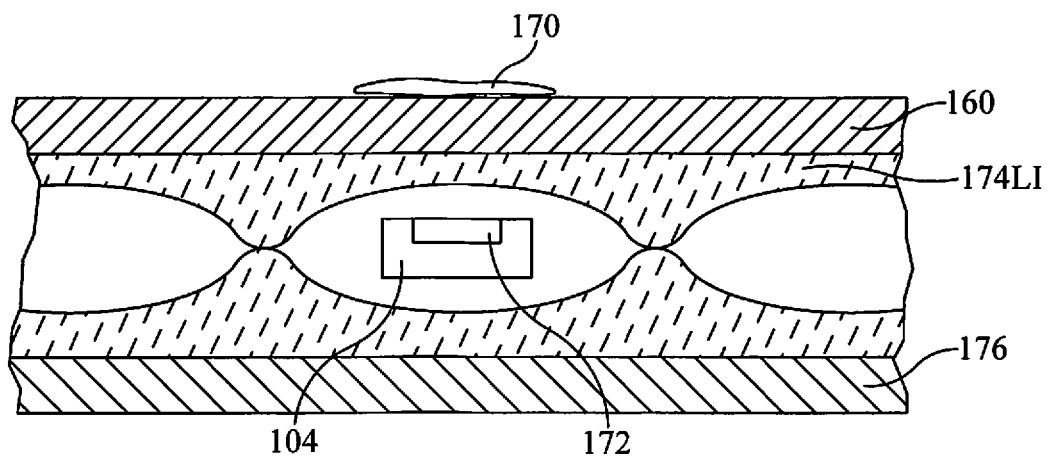
Figure 23:
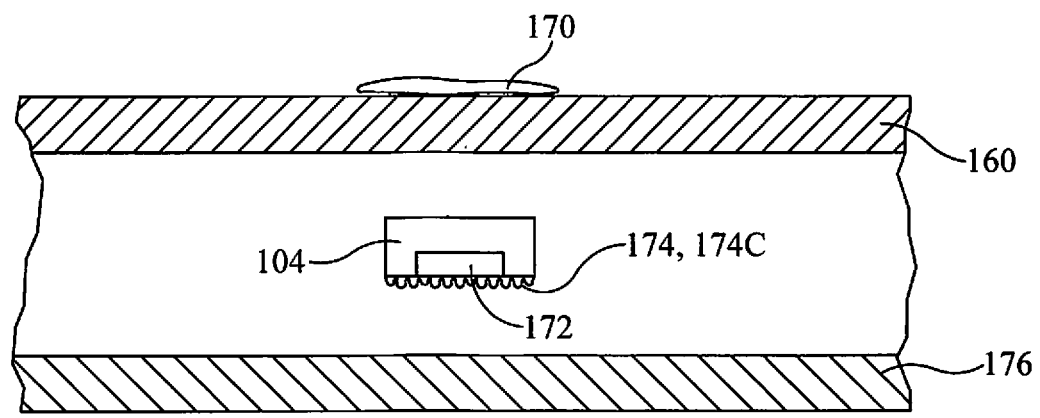
Figure 22A:
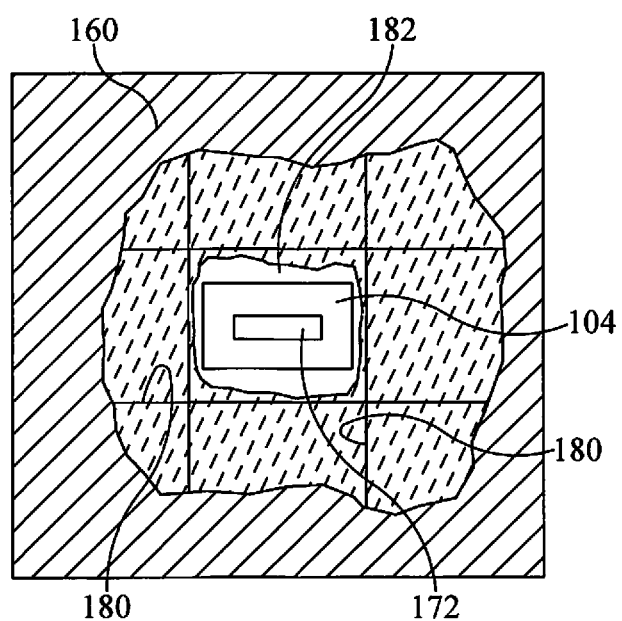

In the embodiment of FIGS. 22 and 22A the reservoir material 174 is a lining 174LI. In the specific embodiment illustrated, lining 174LI also lines base layer 176, and the lining is pinched together at pinch lines 180 to form one or more capsules 182. Sensor 104 resides within the capsule.

In some embodiments the reservoir material may be an absorbent material which retards migration of fluid from the fluid deposition site 170 to the sensor element. Examples of such materials include woven textiles. The porosity of the finished textile can be affected by controlling the parameters of the weaving process during manufacture of the woven textile. Affecting the porosity affects the absorbency of the material. As a result the designer of the moisture detection apparatus can regulate the time lapse between deposition of moisture on the deposition layer 160 and contact between the moisture and moisture responsive element 172. The absorption characteristics of the material 174 also can be used to ensure that the moisture comes into contact with the moisture responsive element 172 only if at least a minimum quantity of moisture is present. That is, a "small" amount of moisture would be completely absorbed by and stored in the material 174 without the moisture being able to migrate the entire distance between deposition site 170 and moisture responsive element 172. By contrast, at least some of a "large" quantity of moisture would be able to migrate the entire distance between deposition site 170 and moisture responsive element 172.

Specific examples of materials from which the absorbent reservoir material may be made include polyester, cotton and polyamide materials.

In some embodiments the reservoir material 174 may be a material which initially acts as a barrier but then dissolves when exposed to moisture in order to retard migration of the moisture from the fluid deposition site 170 to the moisture responsive element 172 until dissolution of the material is complete enough to expose the moisture responsive element to the fluid. An example of such a material is a polymer with the chemical formula: $-(CH_2-CHOR)_n-$ where R is $-H$ or $-COCH_3$. The foregoing chemical formula is the formula for one type of polymer known as polyvinyl alcohol which is also referred to as PVA or PVOH.

The dissolution characteristics of the dissolvable material 174 enables the designer of the moisture detection apparatus to regulate the time lapse between deposition of moisture on the deposition layer 160 and contact between the moisture and moisture responsive element 172. For example a material that dissolves quickly will shorten the time lapse whereas a material that dissolves slowly will lengthen the time lapse. The dissolution characteristics of the material 174 also can be used to ensure that the moisture comes into contact with the moisture responsive element 172 only if at least a minimum quantity of moisture is present. That is, a "small" amount of moisture may be insufficient to dissolve enough of the material 174 to expose moisture responsive element to the moisture. By contrast, a "large" quantity of moisture would be able to effect sufficient dissolution and come into contact with moisture responsive element 172.

Directional Architecture—Capillary.

Figure 24:
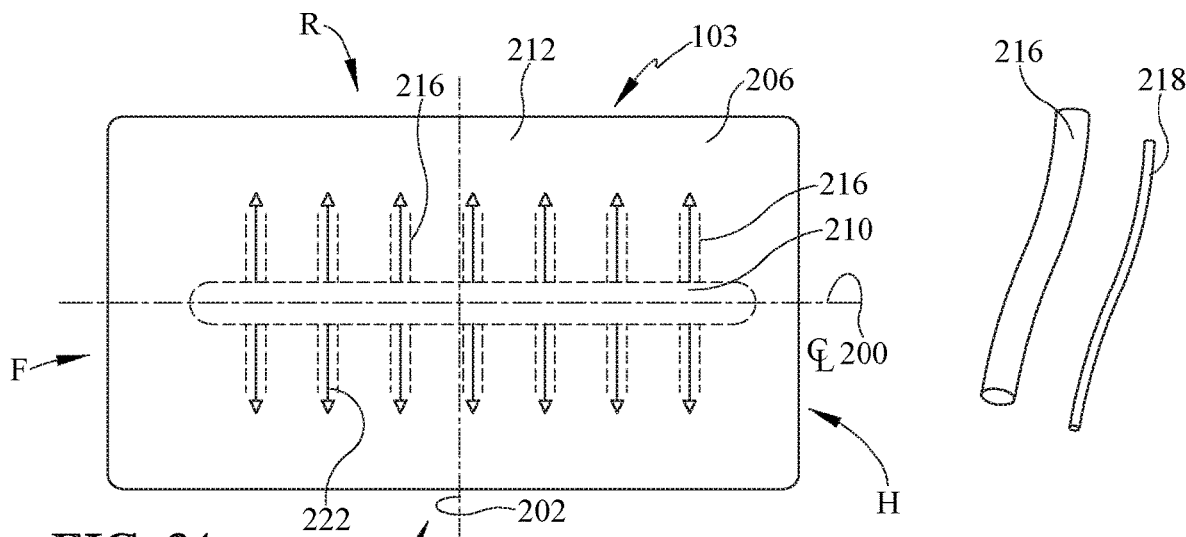
FIGS. 24-26 show variants of an architecture for a moisture handling apparatus, which may be an incontinence pad, in which a capillary property directs moisture from a source to a destination.
Figure 25:
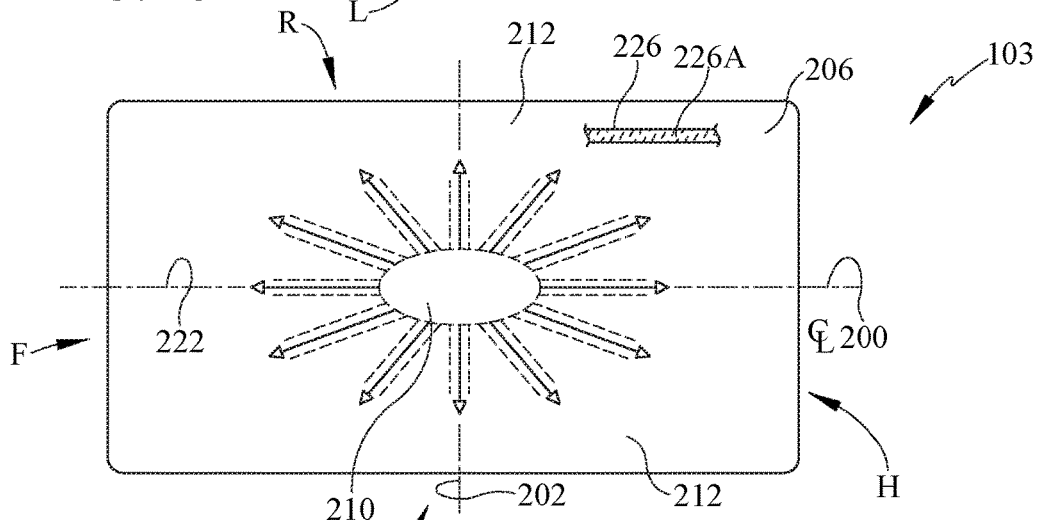
Figure 26:
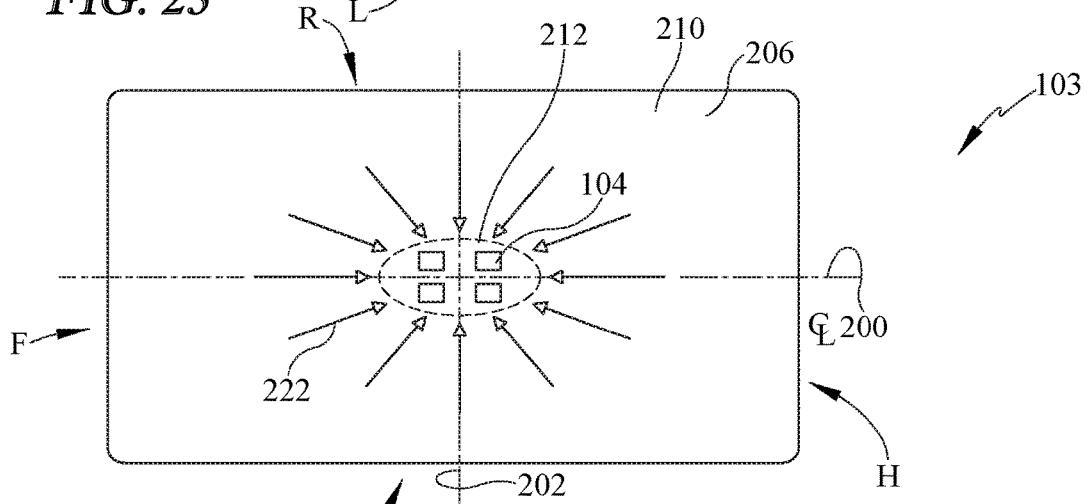

FIGS. 24-26 show variants of an architecture for a moisture handling apparatus, which may be an incontinence pad. The illustrations illustrate a pad-like apparatus having a head end H, a foot end F longitudinally spaced from the head end, a left side L and right side R laterally spaced from the left side. The illustrations also show longitudinally and laterally extending centerlines 200, 202. The apparatus comprises a sheet 206 of material having a capillary property for encouraging moisture migration from a source zone 210 to a destination zone 212.

As seen in FIG. 24 the capillary property may be imparted to the apparatus by capillary tubes 216, or by capillary fibers 218.

The tubes 216 or fibers 218 are spatially arranged or oriented, and therefore the capillary property is spatially arranged or oriented, so as to encourage moisture migration from source zone 210 to destination zone 212.

In the example embodiment of FIG. 24 the source zone 210 is an inboard zone (within dashed lines) whose longitudinal dimension substantially exceeds its lateral dimension. Zone 210 is approximately laterally centered on centerline 200. Destination zone 212 is the outboard perimetral region between the point of fluid flow arrows 222 and the lateral edges of the pad. Alternatively the destination zone may be any zone of the apparatus outside the source zone. As used herein the term "inboard" refers to locations relatively remote from the edges of the bed whereas "outboard" refers to locations relatively closer to the edges of the bed. The capillary property is arranged to define one or more capillary pathways (suggested by the fluid flow arrows) extending substantially exclusively laterally from the source zone to the destination zone. Each flow arrow may be considered to represent a capillary pathway. Alternatively all the flow arrows extending in either the left or right direction may be considered to be a single pathway. Alternatively all the flow arrows extending all directions may be considered to be a single pathway.

In the embodiment of FIG. 25 the source zone 210 is an oval shaped inboard zone (within dashed lines) Destination zone 212 is the outboard perimetral region between the point of fluid flow arrows 222 and the lateral edges of the pad. Alternatively the destination zone may be any zone of the apparatus outside the source zone. The capillary property is arranged to define one or more capillary pathways extending both laterally and longitudinally from the source zone to the destination zone. The pathways of FIG. 25 may be considered to be radial pathways in that they radiate away from the source zone, i.e. from inboard to outboard.

In the embodiment of FIG. 26 the destination zone 212 is an oval shaped inboard zone (within dashed lines) Source zone 210 is the outboard perimetral region between the origins of fluid flow arrows 222 and the lateral edges of the pad. Alternatively the source zone may be any zone of the apparatus outside the destination zone. The capillary property is arranged to define one or more capillary pathways extending both laterally and longitudinally from the source zone 210 to the destination zone 212. The pathways of FIG. 26 may be considered to be radial pathways in that they radiate toward the destination zone, i.e. from outboard to inboard.

The arrangement of FIGS. 24-25 may be useful for drawing moisture away from an occupant lying on the apparatus, for example for removing urine from the site of an incontinence accident. The arrangement of FIG. 26 may be useful for directing the moisture toward a sensor 104, such as an RFID technology based sensor, which is responsive to the moisture.

In another variant the destination zone includes an indicator responsive to the moisture. For example the destination zone may be constructed of a material that changes color in response to contact with urine and/or other fluids of interest or may include a decal that is similarly color responsive to urine and/or other fluids of interest.

In another variant the destination zone includes a collector or may be a collector for collecting the migrated moisture. Such a collector 226 is shown schematically in FIG. 25 as an absorbent material 226A.

The material of which the sheet of material 206 is made is a microfiber. A microfiber has a lineic mass of less than about 1 g/10 km, a diameter of less than about 9 micrometers, or both.

The above described apparatus could be part of a system which includes a processor for detecting or analyzing fluid that comes in contact with a sensor 104 in destination zone 112.

Directional Architecture—Hydroaffinity.

Figure 27:
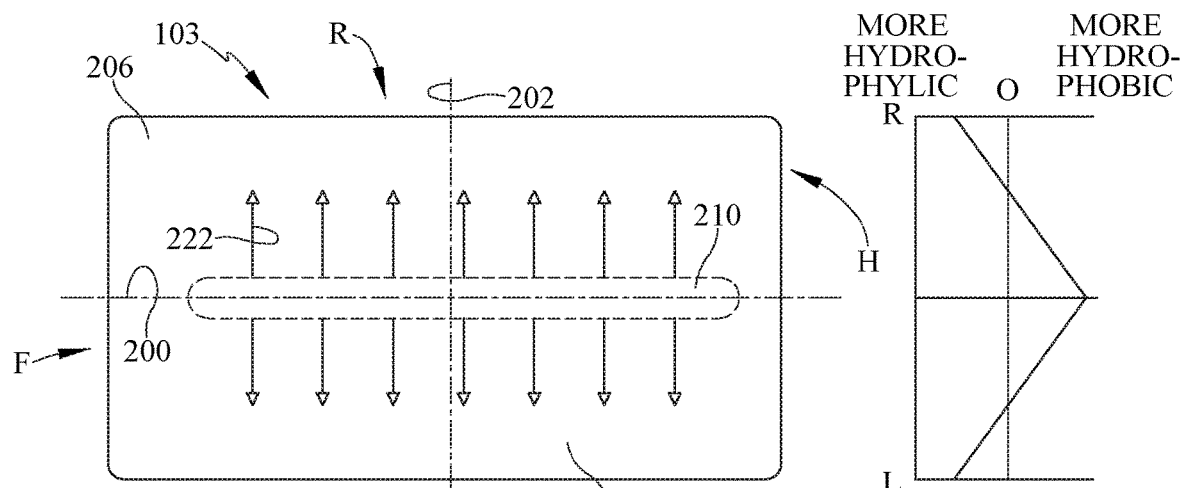
FIGS. 27-29 show variants of an architecture for a moisture handling apparatus, which may be an incontinence pad in which the pad has a hydroaffinity property for directing moisture from a source to a destination.
Figure 28:
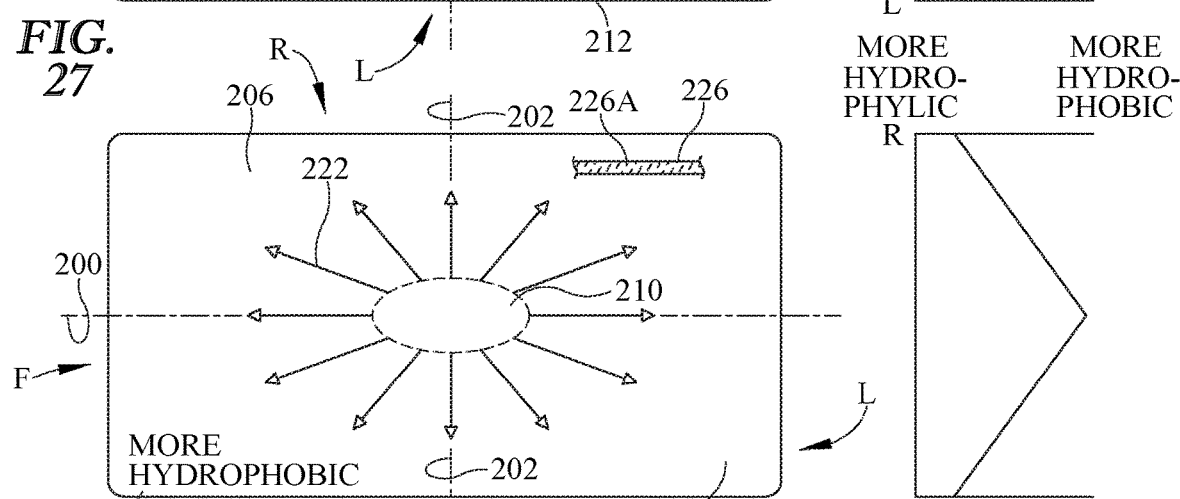
Figure 29:
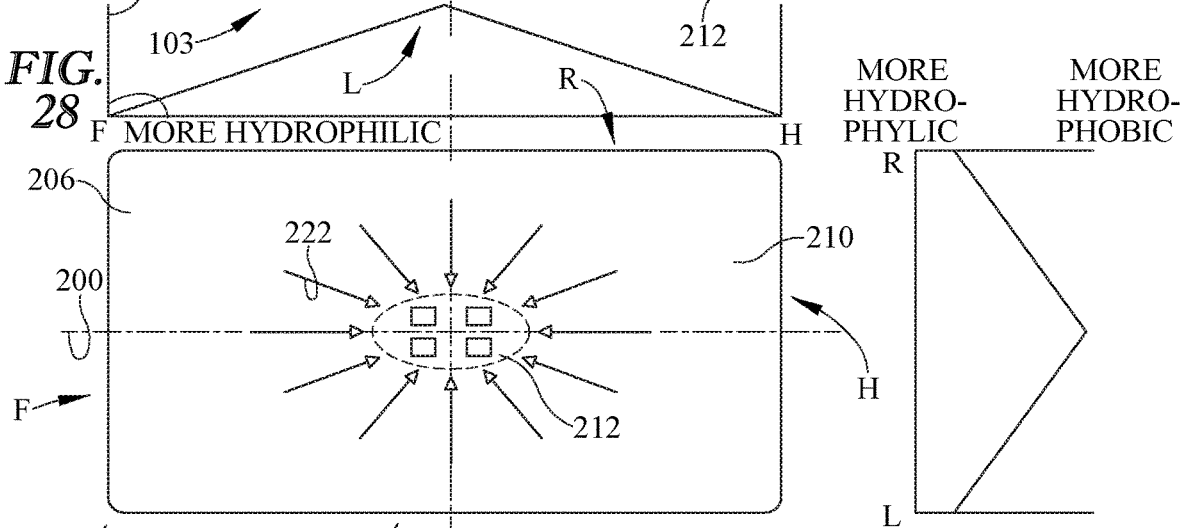

FIGS. 27-29 show variants of an architecture for a moisture handling apparatus, which may be an incontinence pad. The illustrations illustrate a pad-like apparatus having a head end H, a foot end F longitudinally spaced from the head end, a left side L and right side R laterally spaced from the left side. The illustrations also show longitudinally and laterally extending centerlines 200, 202. The apparatus comprises a sheet 206 of material having a hydroaffinity property for encouraging moisture migration from a source to a destination. "Hydroaffinity" as used herein refers to the degree to which the material is hydrophilic, hydrophobic, or some combination of hydrophilic and hydrophobic, such as exhibiting a hydrophillic/hydrophobic gradient. The hydroaffinity property encourages moisture migration from a source zone 210 to a destination zone 212.

The hydroaffinity property is spatially arranged or oriented so as to encourage moisture migration from the source zone 210 to the destination zone 212.

In the example embodiment of FIG. 27 the source zone 210 is an inboard zone (within dashed lines) whose longitudinal dimension substantially exceeds its lateral dimension. Zone 210 is approximately laterally centered on centerline 200. Destination zone 212 is the outboard perimetral region between the points of fluid flow arrows 222 and the lateral edges of the pad. Alternatively the destination zone may be any zone of the apparatus outside the source zone. As used herein the term "inboard" refers to locations relatively remote from the edges of the bed whereas "outboard" refers to locations relatively closer to the edges of the bed. The hydroaffinity property is arranged to define one or more fluid migration pathways (suggested by the fluid flow arrows 222) extending substantially exclusively laterally from the source zone to the destination zone. Each flow arrow may be considered to represent a fluid migration pathway. Alternatively all the flow arrows extending in either the left or right direction may be considered to be a single fluid migration pathway. Alternatively all the flow arrows extending all directions may be considered to be a single fluid migration pathway. FIG. 27 includes a graph whose abscissa axis represents the left to right dimension of the apparatus 103 and whose ordinate axis shows a gradation of hydroaffinity. The graph shows that the sheet of material is relatively more hydrophobic in the vicinity of centerline 200 and is more hydrophilic at the left and right lateral edges.

In the embodiment of FIG. 28 the source zone 210 is an elongated oval shaped inboard zone (within dashed lines) Destination zone 212 is the outboard perimetral region between the points of fluid flow arrows 222 and the lateral edges of the pad. Alternatively the destination zone may be any zone of the apparatus outside the source zone. The hydroaffinity property is arranged to define one or more fluid migration pathways extending both laterally and longitudinally from the source zone to the destination zone. The pathways of FIG. 28 may be considered to be radial pathways in that they radiate away from the source zone, i.e. from inboard to outboard. FIG. 28 includes graphs similar to that of FIG. 27 showing a gradation of hydroaffinity in both the lateral and longitudinal directions. One graph shows that the sheet of material is relatively more hydrophobic in the vicinity of centerline 200 and is more hydrophilic at the left and right lateral edges. The other graph shows that the sheet of material is relatively more hydrophobic in the vicinity of centerline 202 and is more hydrophilic at the head and foot edges.

In the embodiment of FIG. 29 the destination zone 212 is an oval shaped inboard zone (within dashed lines) Source zone 210 is the outboard perimetral region between the origins of fluid flow arrows 222 and the lateral edges of the pad. Alternatively the source zone may be any zone of the apparatus outside the destination zone. The hydroaffinity property is arranged to define one or more fluid migration pathways extending both laterally and longitudinally from the source zone 210 to the destination zone 212. The pathways of FIG. 29 may be considered to be radial pathways in that they radiate toward the destination zone, i.e. from outboard to inboard. FIG. 29 includes graphs similar to those of FIG. 28 but with an opposite gradation of hydroaffinity to account for the fact that the destination zone is an inboard zone and the source zone is an outboard zone. The graphs show that the sheet of material is relatively more hydrophilic in the vicinity of centerline 200 and more hydrophobic at the left and right lateral edges and that the sheet of material is relatively more hydrophilic in the vicinity of centerline 202 and is more hydrophobic at the head and foot edges.

The arrangement of FIGS. 27-28 may be useful for drawing moisture away from an occupant lying on the apparatus, for example for removing urine from the site of an incontinence accident. The arrangement of FIG. 29 may be useful for directing the moisture toward a sensor 104, such as an RFID technology based sensor, which is responsive to the moisture.

In another variant the destination zone includes an indicator responsive to the moisture. For example the destination zone may be constructed of a material that changes color in response to contact with urine and/or other fluids of interest or may include a decal that is similarly color responsive to urine and/or other fluids of interest.

In another variant the destination zone includes a collector or may be a collector for collecting the migrated moisture. Such a collector 226 is shown schematically in FIG. 29 as an absorbent material 226A.

As seen from the foregoing explanation and illustrations the hydroaffinity property is arranged to be more hydrophobic at the source zone and more hydrophilic at the destination zone.

The above described apparatus could be part of a system which includes a processor for detecting or analyzing fluid that comes in contact with a sensor 104 in destination zone 112.

Visual Indicators—Color Changing.

Figure 30:
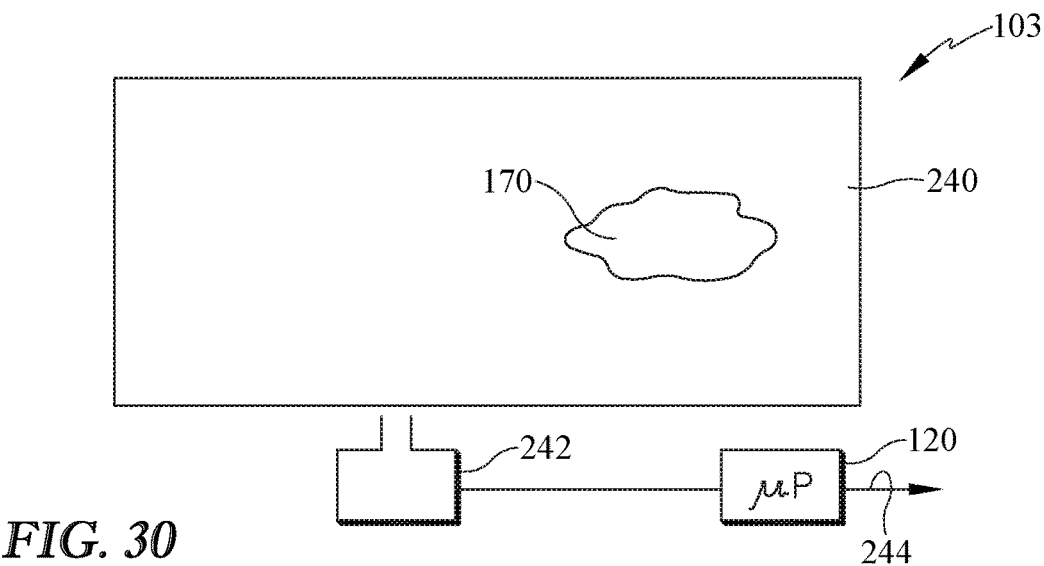
FIGS. 30-32 show variants of an architecture for a color changing moisture detecting system, which may be an incontinence pad.
Figure 31:
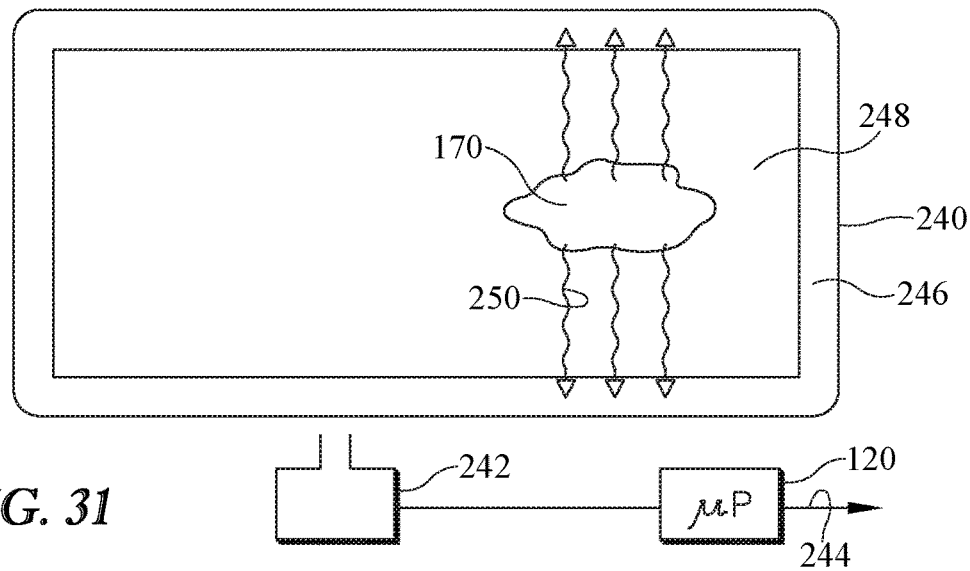
Figure 32:
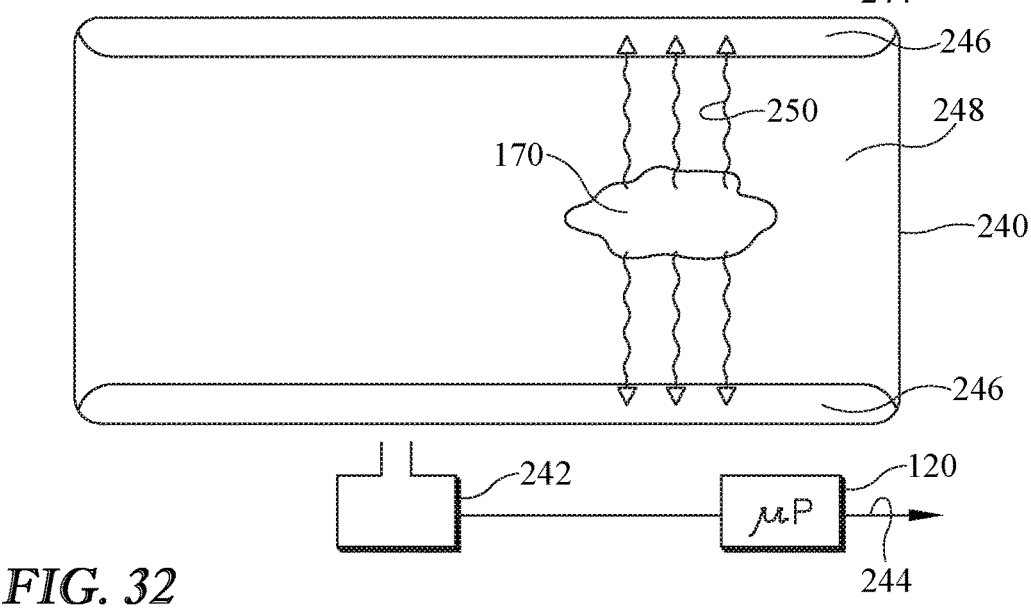

FIGS. 30-32 show variants of an architecture for a moisture detecting system, which may be an incontinence pad 103. Referring principally to FIG. 30, the moisture detecting system comprises a sheet of material 240 adapted to change color in response to the presence of moisture 170. The system also comprises a camera 242 or other color detection circuitry for observing the color change or lack thereof. The absence of a color change is a limit case which may be considered to be a "null" color change. The system also includes a controller 120 in communication with the camera. The controller processes the observations of the camera and issues a response 244. In the case of the absence of color change the response may be a null response. If a color change occurs the response may be a signal which activates an alerting or reporting system and/or records the event, such as an incontinence event, in an electronic medical record.

FIGS. 31-32 show a variant in which sheet 240 has an indicator portion 246 adapted to change color in response to the presence of moisture and a transport portion 248 adapted to transport moisture from a site of deposition thereof 170 to the indicator portion 246 as indicated by the fluid migration arrows 250. In FIG. 31 the indicator portion 246 is a perimetral portion 246. In FIG. 32 the indicator portion 246 is an edge portion 246 along one or both lateral sides of sheet 240.

The embodiment of FIG. 30 and may include features such as those of FIGS. 24-29 to transport moisture from a deposition site 170 to another site. The embodiments of FIGS. 31-32 may include features such as those of FIGS. 24-29 to transport moisture from a deposition site 170 at the transport portion 248 to the indicator portion 246 and to help transport moisture further into the interior of the indicator portion.

Visual Indicators—UV from any Source+Camera.

Figure 33:
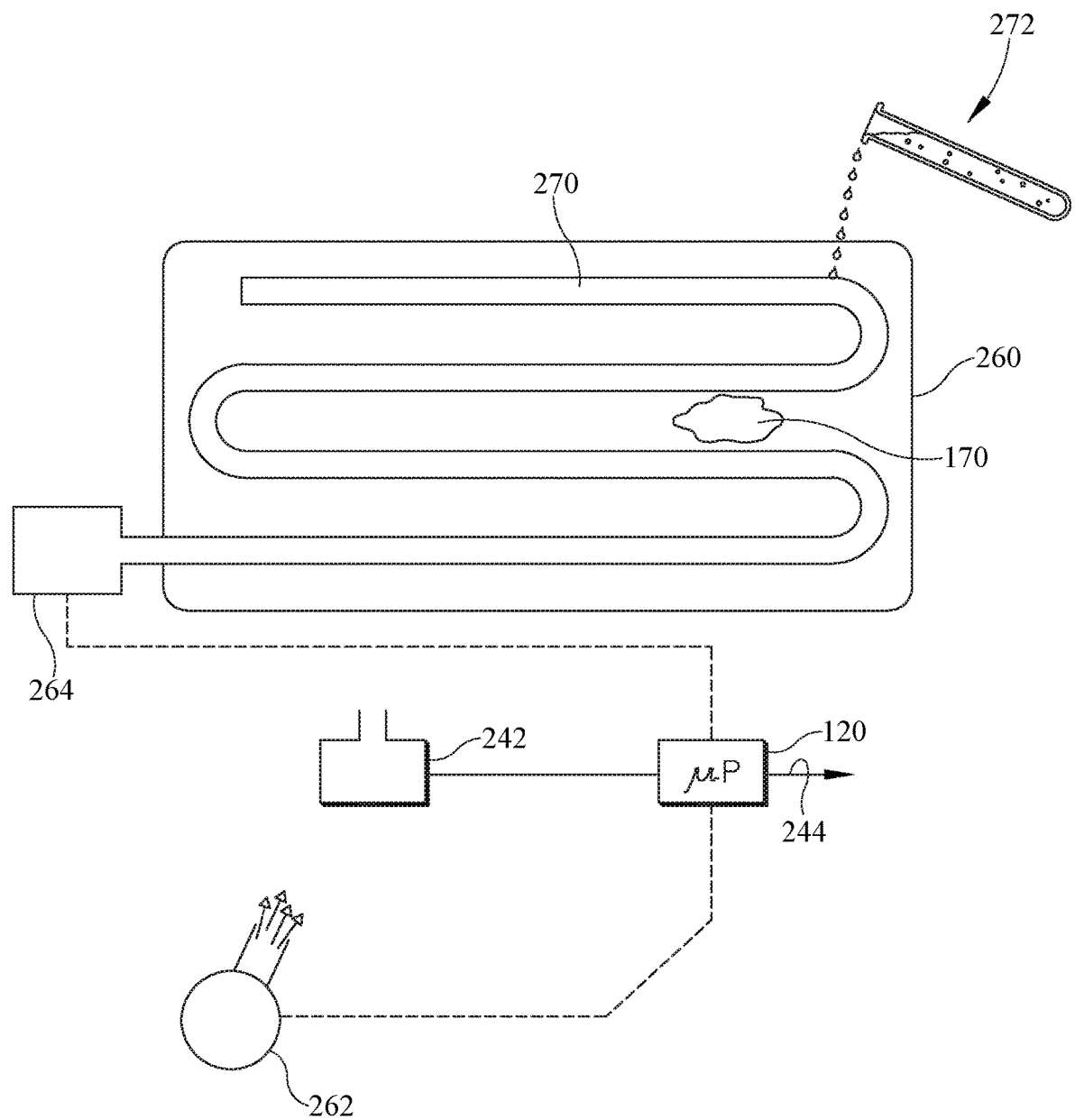
FIG. 33 shows an architecture of another moisture detecting system, which may be an incontinence pad, and which indicates moisture presence as a result of exposure to ultraviolet radiation and which may use a camera to detect changes indicative of the presence of moisture on a previously dry surface.

FIG. 33 shows an architecture of another moisture detecting system, which may be an incontinence pad 103. The detecting system comprises a sheet of material 260 which receives the moisture 170. The system also includes a source of ultraviolet radiation adapted to expose at least a target portion of the sheet of material to ultraviolet radiation. In one embodiment the source is an external source 262. In another embodiment the source is an integrated or on-board source 264. Source 264 includes a light tube 270 that extends through the pad.

The system also includes a camera 242 or other emission detection circuitry for observing emission of radiation or lack thereof in response to the presence of moisture 170 within the target region and excitation of the moisture by the ultraviolet radiation. The absence of emitted radiation in response to the ultraviolet radiation is a limit case which may be considered to be a "null" emission.

The system also includes a controller 120 in communication with the camera and with the ultraviolet light source 262 or 264/270. The controller processes the observations of emitted radiation or a change in emitted radiation made by camera 242 (the emissions being in response to the ultraviolet excitation) and issues a response 244. In the case of the absence of emission or absence of a change in emission the response may be a null response. If an emission or change of emission is detected, the response may be a signal 244 which activates an alerting or reporting system and/or records the event, such as an incontinence event, in an electronic medical record.

The controller may periodically activate and deactivate the source of ultraviolet radiation 262 or 264/270. Alternatively the source may be manually activated at the discretion of a caregiver.

Sheet of material 260 may be chemically treated 272 to intensify the radiated emission thereby making it more readily detectable.

Visual Indicators—UV from Light Tube.

In another embodiment camera 242 and processor 244 are absent and the system comprises the sheet of material 260 which receives the moisture and a source of ultraviolet radiation comprising an ultraviolet radiation generator 264 and a light tube 270 that extends through the sheet for distributing the ultraviolet radiation to the target region thereby exposing at least a target portion of the sheet of material to the ultraviolet radiation.

FIG. 33 shows an ultraviolet excited pad architecture similar to the color changing pad architecture of FIG. 30. However the ultraviolet excited pad architecture could be some other architecture such as that of FIGS. 31 and 32 which have both an indicator portion and a transport portion.

Multifunctional Sensor Pad.

Figure 34:
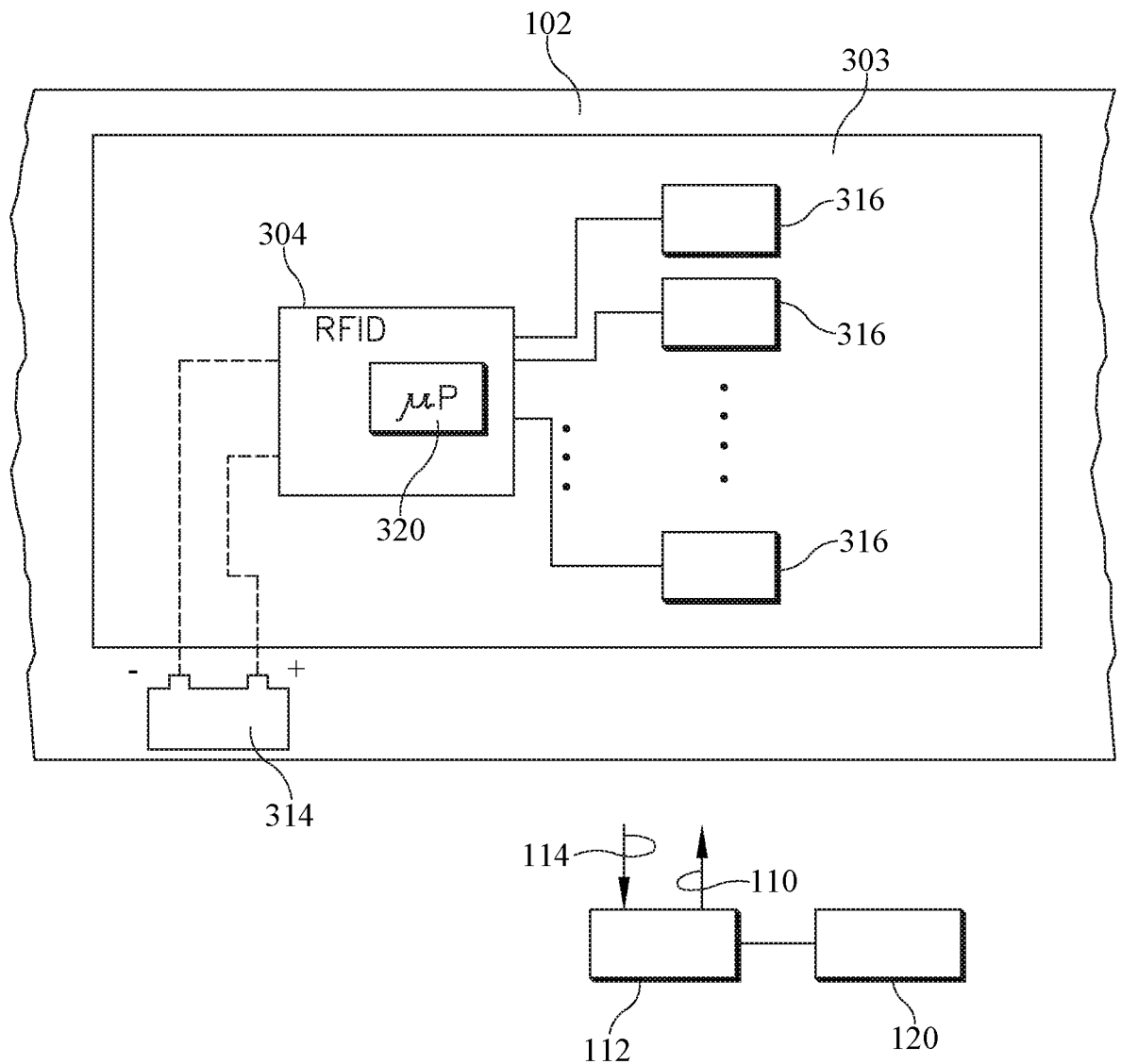
FIG. 34 shows a sensor pad having an RFID tag with a processor adapted to process inputs obtained from multiple sensors which have different parameter sensing capabilities.

FIG. 34 shows a sensor pad 303 resting on a mattress 102 of a bed. The bed and pad are associated with an occupant or patient assigned to the bed. The sensor pad comprises at least one RFID tag 304. Tag 304 includes a processor such as microprocessor 320 adapted to process inputs obtained from multiple sensors 316 even though the sensor have disparate sensing capabilities. Processor 320 receives the input from sensors 316 in the form of electric or electromagnetic signals. For example sensors 316 may have sensing capabilities such as moisture sensing, odor sensing, chemical identity sensing, chemical property sensing, interface pressure sensing, sound sensing, and vital sign sensing to detect vital signs (e.g. blood pressure, heart rate, respiration rate, skin temperature, internal temperature) of a patient associated with the pad. On a given pad 303 sensors may all have the same sensing capability (e.g. interface pressure sensing) or a pad may have sensors 316 for sensing two or more parameters. The technology upon which the sensing capability is based may be any suitable technology such as an accelerometer or a vibration sensor or a sensor based on piezoelectric, piezoresistive, capacitive, inductive, or resistive principles.

Certain sensors may be able to sense a parameter of interest directly and report the value of the sensed parameter to processor 320 by way of an electric or electromagnetic signal. Other sensors may respond to the sensed parameter in a way that requires interpretation by the processor 320.

As already noted in this application, RFID sensors can be employed to sense moisture, for example urine deposited on the mat as the result of patient incontinence. Nevertheless sensors 316 may also be used to sense moisture. Alternatively, the RFID can be relied on for its ability to indicate the presence of moisture as a result of its moisture dependent properties, and the other sensors 316 may be relied on for their capability to sense parameters other than moisture.

Battery 314 is optional and may be included to enable RFID tag 304 to actively broadcast a signal.

Sensor/Switch Closed by Dissolution of Insulator.

FIGS. 35-36 show a sensor pad which may be an incontinence pad 103. The pad includes a sensor 330 comprising a switch 332 having a first terminal 334, a second terminal 336, and an electrically conductive bridge 340 at one end of a shank 342. The sensor also includes a fuse 346. The illustrated fuse is a patch of electrically insulative material interposed between bridge 340 and terminals 334, 336. A coil spring 350 urges the bridge against the fuse.

The fuse, and therefore the switch, has an open state (FIG. 35) in which the fuse impedes the establishment of an electrical connection between the terminals. The fuse, and therefore the switch, also has a closed state (FIG. 36) in which the fuse enables the establishment of the electrical connection in response to a stimulus acting on the fuse by allowing the bridge to contact the terminals. In the illustrated embodiment the fuse is dissolvable by urine and the stimulus is the presence of urine 352 on the fuse. The urine dissolves the fuse and, as a result, spring 350 urges bridge 340 into contact with terminals 334, 336.

FIG. 37 shows an alternative embodiment in which the fuse is a membrane 356 which counteracts the force of spring 350 until contact with urine dissolves the membrane.

Figure 38:
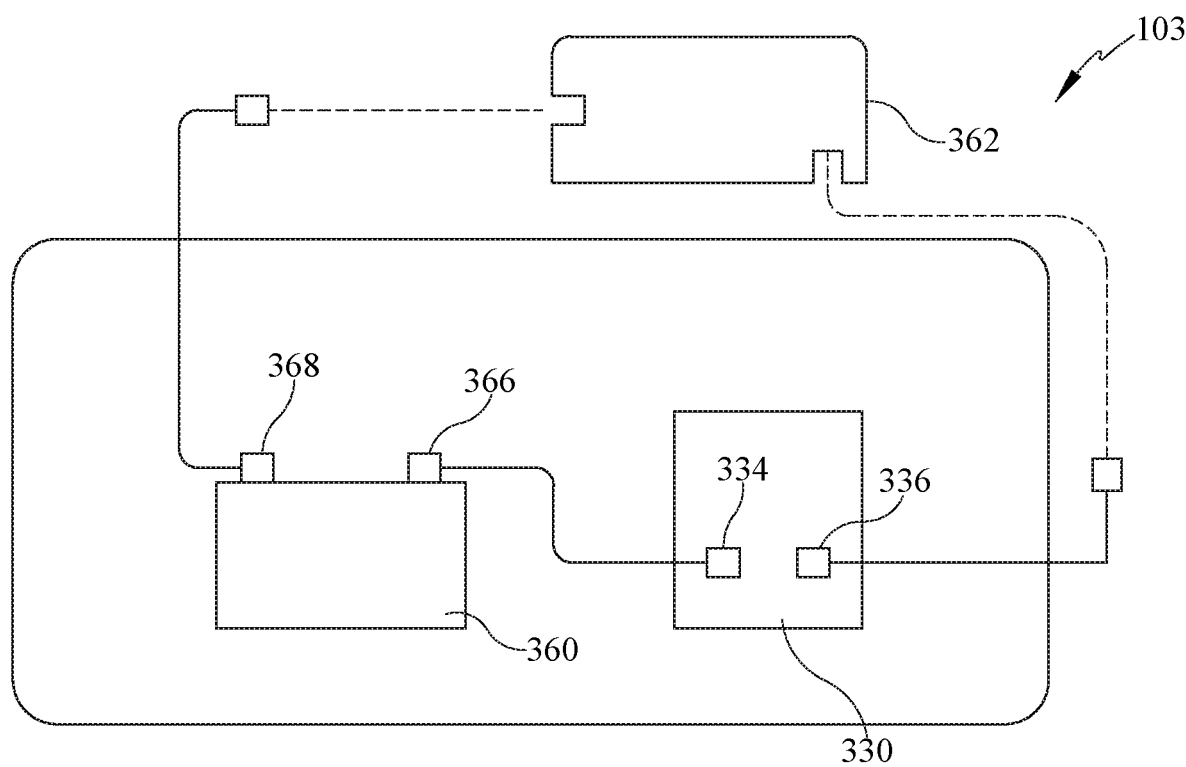
FIGS. 38-39 are alternative embodiments of the system of FIGS. 35-36.
Figure 39:
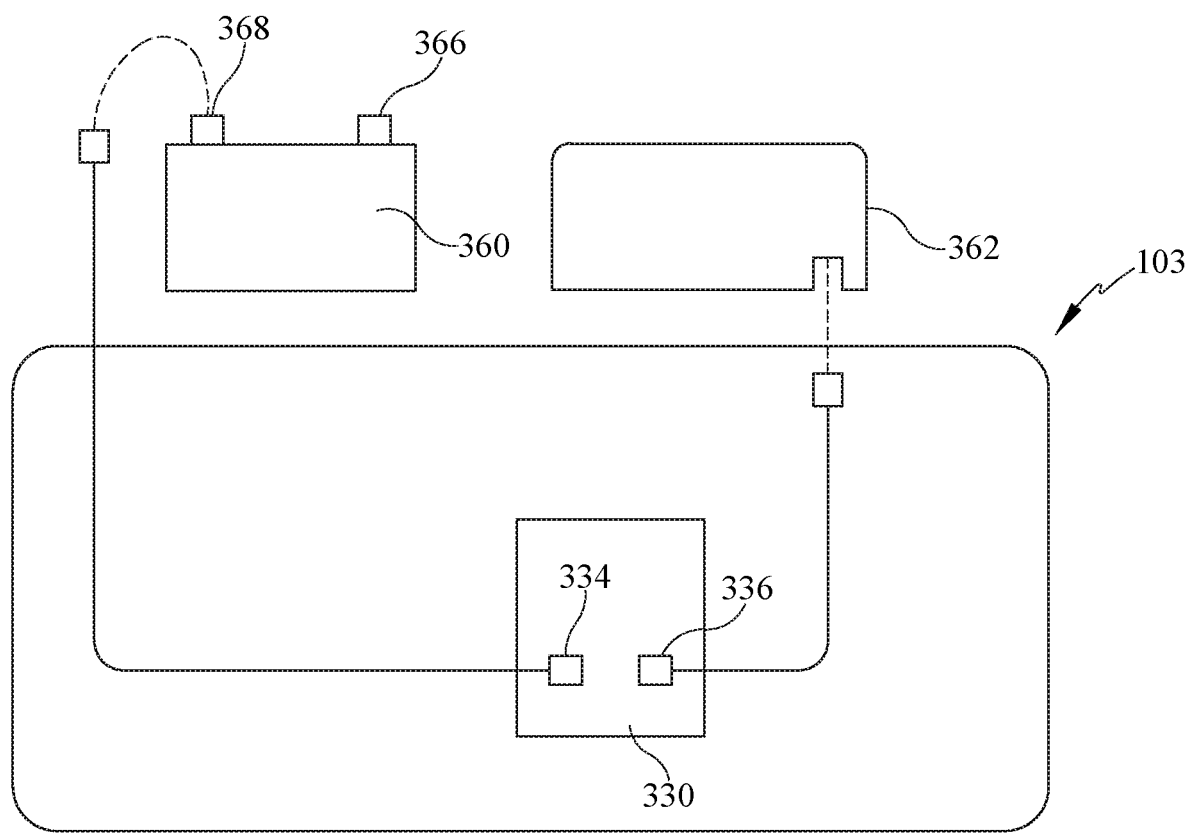

Returning to FIG. 35, one of the sensor switch terminals 334 is connected to a battery 360 and the other of the sensor switch terminals 336 is connected to a load 362. Load 362 is an alarm that responds to completion of the circuit as a result of the fuse having dissolved. The alarm may be an audible alarm or a visible alarm. As seen in FIG. 35 switch 332, battery 360 and load 362 are all components of pad 103. In another embodiment (FIG. 38) pad 103 includes only sensor 330 and battery 360. One of the battery terminals 366 is connected to terminal 334 of the sensor switch and the other of the battery terminals 368 is connectable to the load 362, which is not a component of pad 103. Switch terminal 336 is also connectable to load 362. In another embodiment (FIG. 39) pad 103 includes only sensor 330. Switch terminal 334 is connectable to battery terminal 368. Switch terminal 336 is connectable to load 362.

The foregoing example the fuse is dissolvable in response to contact with urine. Accordingly, the presence of urine in contact with the fuse is the stimulus. However the fuse can be configured to respond to a stimulus other than contact with urine, such as temperature, pressure and vibration, in which case the mechanism responsible for the change of state of the sensor switch may be something other than dissolution.

RFID with Antenna Segments United by Dissolution of Insulator.

Figure 40:
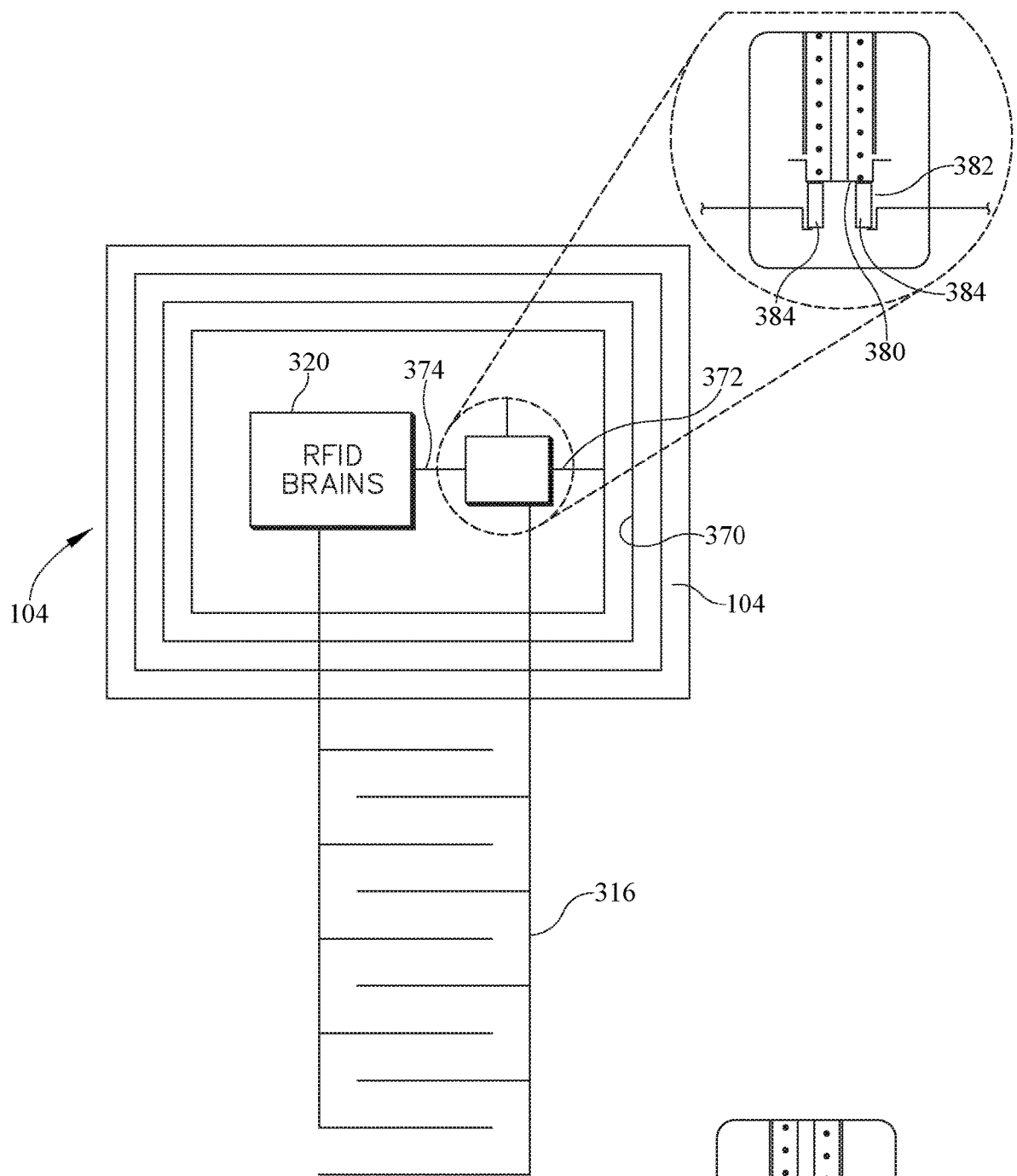
FIGS. 40-41 are schematic views showing a sensor in the form of an RFID tag having two antenna segments and which includes a bridge which is transitionable between a first state in which a separator impedes unification of the segments and a second state in which the separator does not impede unification of the segments and in which transition from the first state to the second state occurs in response to an agent acting on the separator.
Figure 41:
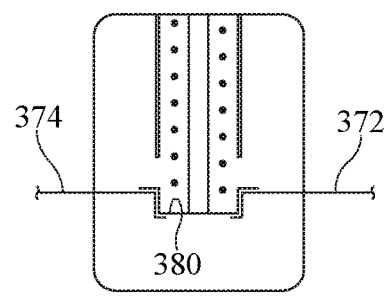

FIGS. 40-41 shows a sensor 104 in the form of an RFID tag, the tag includes an antenna 370 having at least two antenna segments 372, 374. The RFID tag also includes a bridge 380 adapted to unite the segments, and a separator 382 which is transitionable between a first state (inset of FIG. 40) in which the separator impedes unification of the antenna segments and a second state (FIG. 41) in which the separator does not impede unification of the antenna segments. In the illustrated embodiment the separator is a pair of short pillars 384. Transition from the first state (inset of FIG. 40) to the second state (FIG. 41) occurs in response to an agent acting on the separator. For example the agent may be urine which causes the separator to dissolve when the urine comes into contact with the separator. Alternatively the sensor can be configured to respond to an agent other than contact with urine, such as temperature, pressure and vibration, in which case the mechanism responsible for the change of state of the sensor switch may be something other than dissolution.

Sensor 104 of FIG. 40 may be of the type shown in FIG. 34 which includes a processor 320 in communication with adjunct sensors 316 and adapted to process inputs obtained from multiple adjunct sensors even though the adjunct sensors have disparate sensing capabilities.

Example Clauses

RSSI Based Method of Sensor Interrogation for Detecting Incontinence or Other Moisture Caused Abnormality Clause 1. A method of interrogating a sensor to detect the presence of moisture on an occupant support comprising: A) providing a moisture responsive sensor in a surveillance zone of the occupant support, the sensor being tuned to a center frequency; B) exciting the sensor with an electromagnetic signal having a frequency approximately equal to the center frequency; C) monitoring for a center frequency response from the sensor; D) comparing the center frequency response to an expected center frequency response; and E) if the center frequency response compares favorably to an expected center frequency response, issuing a first output consistent with the favorable comparison.

Clause 2. The method of clause 1 comprising: F) if the center frequency response does not compare favorably with the expected center frequency response, exciting the sensor with one or more electromagnetic test signals having test frequencies different than the center frequency and monitoring for a test frequency response at each test frequency and, if the test frequency response from the sensor compares favorably to an expected test frequency response corresponding to the test frequency, issuing a second output consistent with the favorable comparison between the test frequency response and the expected test frequency response corresponding to the test frequency; and G) if the test frequency response from the sensor does not compare favorably to an expected test frequency response corresponding to the test frequency at any of the test frequencies, issuing a third output consistent with the unfavorable comparison between the test frequency response and the expected test frequency response corresponding to the test frequency.

Clause 3. The method of clause 2 wherein the output issued at step F is issued in response to the favorable comparison without first exciting the sensor at any other test frequencies.

Clause 4. The method of clause 2 wherein the output issued at step F in response to the favorable comparison is not issued until the sensor has been excited at at least one frequency other than the test frequency that yielded the favorable comparison.

Clause 5. The method of clause 1 wherein the electromagnetic signals are radio frequency signals.

Clause 6. The method of clause 1 wherein the sensor is an RFID sensor.

Clause 7. The method of clause 1 wherein the first output is an indication that an incontinence pad is present and no incontinence is detected.

Clause 8. The method of clause 2 wherein the second output is an indication that an incontinence pad is present and incontinence is detected and wherein the third output is an indication that an incontinence pad is absent or a fault has occurred.

System for Detecting Incontinence or Other Moisture Caused Abnormality

Clause 101. A system for detecting the presence of moisture on an occupant support comprising: a moisture responsive sensor in a surveillance zone of the occupant support, the sensor being tuned to a center frequency; a transceiver adapted to excite the sensor with an electromagnetic signal having a frequency approximately equal to the center frequency and to monitor for a center frequency response from the sensor; a processor adapted to compare the center frequency response to an expected center frequency response; and to issue a first output if the center frequency response compares favorably to an expected center frequency response.

Clause 102. The system of clause 101 wherein the processor is also adapted to respond as set forth below if the center frequency response does not compare favorably with the expected center frequency response: A) command the transceiver to excite the sensor with one or more electromagnetic test signals having test frequencies different than the center frequency; B) compare the test frequency response to an expected test frequency response corresponding to the test frequency; and C) if the test frequency response from the sensor compares favorably to an expected test frequency response corresponding to the test frequency, issuing a second output consistent with the favorable comparison between the test frequency response and the expected test frequency response corresponding to the test frequency; and D) if the test frequency response from the sensor does not compare favorably to an expected test frequency response corresponding to the test frequency at any of the test frequencies, issue a message consistent with the unfavorable comparison between the test frequency response and the expected test frequency response corresponding to the test frequency.

Clause 103. The system of clause 101 wherein the electromagnetic signals are radio frequency signals.

Clause 104. The system of clause 101 wherein the sensor is an RFID sensor.

Clause 105. The system of clause 104 comprising an exposed sensor and a protected sensor.

Plus Multiple or Multiplexed Sensors

Clause 106. The system of clause 101 comprising two or more sensors at least some of which are individual sensors having an antenna.

Clause 107. The system of clause 106 wherein all of the sensors are individual sensors having an antenna.

Clause 108. The system of clause 101 comprising two or more sensors at least some of which are individual antenna components of a sensor assembly.

Clause 109. The system of clause 106 wherein all of the sensors are individual antenna components of a sensor assembly.

Rate of Change Based Method of Sensor Interrogation for Detecting Incontinence or Other Moisture Caused Abnormality.

Clause 201. A method of interrogating a sensor to detect the presence of moisture on an occupant support comprising: A) providing a moisture responsive sensor in a surveillance zone of the occupant support, the sensor being tuned to a center frequency; B) exciting the sensor with an electromagnetic signal having a frequency approximately equal to the center frequency; C) monitoring for a center frequency response from the sensor; D) calculating a rate of change based on the center frequency responses received at different times; E) comparing the rate of change to one or more thresholds; and F) issuing an output depending on the comparison.

Clause 202. The method of clause 201 wherein the calculated rate of change is a function of a change in RSSI over an interval of time.

Clause 203. The method of clause 202 wherein the calculated rate of change is a function of the difference between two excitation frequencies each of which produces a response having approximately equal RSSI values.

Clause 204. The method of clause 201 wherein the electromagnetic signals are radio frequency signals.

Clause 205. The method of clause 201 wherein the sensor is an RFID sensor.

Clause 206. The method of clause 201 wherein the thresholds are TMOIST and TMOVE and wherein the issued output is as set forth in the table below in which the rate of change is denoted as dR/dt:

| Condition | Issued output |
| --- | --- |
| dR/dt < TMOIST | First |
| TMOIST ≤ dR/dt < TMOVE | Second |
| TMOVE ≤ dR/dt | Third |

Clause 207. The method of clause 206 wherein the first output is an indication that an incontinence pad is present and no incontinence is detected, the second output is an indication that an incontinence pad is present and incontinence is detected, and the third output is an indication that an incontinence pad is absent.

Method of Sensor Interrogation for Detecting Incontinence or Other Moisture Caused Abnormality Based on Protected and Exposed Sensors.

Clause 301. A method of interrogating a sensor suite to detect the presence of moisture on an occupant support comprising: A) providing first and second moisture responsive sensors in a surveillance zone of the occupant support, the sensors each being tuned to a center frequency, the first sensor being protected from coming into contact with moisture which may be present in the surveillance zone and the second sensor being exposed to coming into contact with moisture which may be present in the surveillance zone; B) exciting the sensors with an electromagnetic signal having a frequency approximately equal to its center frequency; C) monitoring for a center frequency response from the sensors;

D) comparing the center frequency responses to an expected center frequency response for each sensor; and E) issuing an output depending on the comparison as set forth below:

| Result of comparison (response vs. expected response) for first sensor | Result of comparison (response vs. expected response) for second sensor | Output |
| --- | --- | --- |
| RSSI strong | RSSI strong | no moisture detected |
| RSSI strong | RSSI weak or absent | moisture detected |
| RSSI weak or absent | RSSI strong | fault |
| RSSI weak or absent | RSSI weak or absent | sensor not present or sensor moved or fault |

Clause 302. The method of clause 301 wherein the electromagnetic signals are radio frequency signals.

Clause 303. The method of clause 301 wherein the sensors are RFID sensors.

System for Detecting Incontinence or Other Moisture Caused Abnormality Based on Protected and Exposed Sensors.

Clause 401. A system for detecting the presence of moisture on an occupant support comprising: first and second moisture responsive sensors in a surveillance zone of the occupant support, each sensor being tuned to a center frequency; a transceiver adapted to excite each sensor with an electromagnetic signal having a frequency approximately equal to its center frequency and to monitor for a center frequency response from each sensor; a processor adapted to compare the center frequency response of the first sensor to an expected center frequency response of the first sensor and to compare the center frequency response of the second sensor to an expected center frequency response of the second sensor; and to issue an output depending on the comparison as set forth below:

| Result of comparison (response vs. expected response) for first sensor | Result of comparison (response vs. expected response) for second sensor | Output |
| --- | --- | --- |
| RSSI strong | RSSI strong | no moisture detected |
| RSSI strong | RSSI weak or absent | moisture detected |
| RSSI weak or absent | RSSI strong | fault |
| RSSI weak or absent | RSSI weak or absent | sensor not present or sensor moved or fault |

Clause 402. The method of clause 401 wherein the electromagnetic signals are radio frequency signals.

Clause 403. The method of clause 401 wherein the sensors are RFID sensors.

Clause 404. The method of clause 401 wherein each sensor is tuned to approximately the same center frequency.

Method of Fluid Analysis.

Clause 501. A method of interrogating a sensor to detect the presence of moisture on an occupant support and to analyze moisture which may be present comprising: A) providing a moisture responsive sensor in a surveillance zone of the occupant support, the sensor being tuned to a center frequency; B) exciting the sensor with an electromagnetic signal having a frequency approximately equal to the center frequency; C) monitoring for a center frequency response from the sensor; D) comparing the center frequency response to an expected center frequency response; and E) if the center frequency response compares favorably to an expected center frequency response, issuing a first output consistent with the favorable comparison; and F) if the center frequency response does not compare favorably with the expected center frequency response, exciting the sensor with one or more electromagnetic test signals having test frequencies different than the center frequency and monitoring for a test frequency response at each test frequency and, G) if the test frequency response from the sensor compares favorably to an expected test frequency response corresponding to the test frequency, correlating the test frequency response with a relationship of entity, fluid properties or both and issuing a second output consistent with the favorable comparison between the test frequency response and the expected test frequency response corresponding to the test frequency.

Clause 502. The method of clause 501 wherein: H) if the test frequency response from the sensor does not compare favorably to an expected test frequency response corresponding to the test frequency at any of the test frequencies, issuing a third output consistent with the unfavorable comparison between the test frequency response and the expected test frequency response corresponding to the test frequency.

Clause 503. The method of clause 502 wherein the output issued at step G is issued in response to the favorable comparison without first exciting the sensor at any other test frequencies.

Clause 504. The method of clause 502 wherein the output issued at step G in response to the favorable comparison is not issued until the sensor has been excited at at least one frequency other than the test frequency that yielded the favorable comparison.

Clause 505. The method of clause 501 wherein the first output is an indication that a moisture sensing device is present and no moisture is detected.

Clause 506. The method of clause 501 wherein the second output is an indication that a moisture sensing device is present and moisture is detected and wherein the second output is also an indication of the identity of the fluid, the type of fluid or both as defined by the relationship between test frequency response and fluid identity, fluid properties or both.

Clause 507 The method of clause 502 wherein the third output is an indication that a moisture sensing device is absent or a fault has occurred.

Method for Detecting Incontinence or Other Moisture Caused Abnormality Using Multiple RFID's or Other Sensors or Using Multiplexed RFID's or Other Sensors.

Clause 601. A method of detecting the presence of moisture on an occupant support, displacement of a moisture sensor or both comprising: A) providing two or more moisture responsive sensors in a surveillance zone of the occupant support, the sensors being tuned to a center frequency; B) exciting the sensors with an electromagnetic signal having a frequency approximately equal to the center frequency; C) monitoring for and receiving center frequency responses from the sensors and recording the individual center frequency responses at a time t=0; D) continuing to excite the sensors and to monitor for and receive responses at time t>t0. E) detecting differences in center frequency response for each sensor at one or more times t>0; and F) analyzing the differences in center frequency response to discern moisture presence, sensor displacement or both.

Clause 602. The method of clause 601 wherein the sensors are individual sensors each having an antenna.

Clause 603. The method of clause 601 wherein the sensors are individual antenna components of a sensor assembly.

Clause 604. The method of clause 601 wherein moisture detection is declared as a result of: A) center frequency response from a first set of one or more sensors having become weaker at a time t>0 relative to the center frequency response of the one or more sensors at an earlier time, and B) the response of a second set of sensors which does not include members of the first set having substantially the same response strength at time t>0 than at the earlier time.

Clause 605. The method of clause 601 wherein sensor displacement is declared as a result of center frequency response from substantially all the sensors having become weaker at a time t>0 relative to the center frequency response of the sensors at an earlier time.

Method for Detecting Incontinence or Other Moisture Caused Abnormality Using Multiple RFID's or Other Sensors or Using Multiplexed RFID's or Other Sensors and Based on Highest Return Signal Strength.

Clause 701. A method of detecting the presence of moisture on an occupant support comprising: A) providing two or more moisture responsive sensors in a surveillance zone of the occupant support, the sensors being tuned to a center frequency; B) exciting the sensors with an electromagnetic signal having a frequency approximately equal to the center frequency; C) monitoring for and receiving center frequency responses from the sensors and identifying which sensor returns the strongest response; D) continuing to excite the sensors and to monitor for and receive center frequency responses; E) monitoring the sensors for changes in return signal strength in response to the continuing excitation relative to the excitation at step B; and F) analyzing the return signal strengths from the excitation at step B in comparison to those from the excitations at step D and: G) if the analysis of step E demonstrates that the return signal strength of the identified sensor has diminished over time, further analyzing the differences in center frequency response of one or more sensors other than the identified sensor to detect moisture presence or sensor displacement or both.

System for Detecting Incontinence or Other Moisture Caused Abnormality Using Multiple RFID's or Other Sensors or Using Multiplexed RFID's or Other Sensors.

Clause 801. A system for detecting the presence of moisture on an occupant support or displacement of a sensor or both comprising: multiple moisture responsive sensors spatially distributed in a surveillance zone of the occupant support, each sensor being tuned to a center frequency and having at least one antenna; a transceiver adapted to excite the sensors with an electromagnetic signal having a frequency approximately equal to the center frequency and to monitor for a center frequency response from the sensor; a multiplexer in communication with each antenna and with the transceiver; a processor adapted to command the transceiver to excite the sensors and to compare the center frequency response of each sensor to an expected center frequency response to detect the presence of moisture on the occupant support or displacement of a sensor or both.

Clause 802. The system of clause 801 wherein at least some of the sensors are individual sensors having an antenna and the processor is adapted to command the multiplexer to acquire response signals from each antenna.

Clause 803. The system of clause 802 wherein all of the sensors are individual sensors having an antenna and the processor is adapted to command the multiplexer to acquire response signals from each antenna.

Clause 804. The system of clause 801 wherein at least some of the two or more sensors are individual antenna components of a sensor assembly and the processor is adapted to command the multiplexer to acquire response signals from each antenna component.

Clause 805. The system of clause 804 wherein all of the two or more sensors are individual antenna components of a sensor assembly and the processor is adapted to command the multiplexer to acquire response signals from each antenna component.

Hybrid Incontinence Detection System

Clause 901. A system for detecting the presence of moisture on an occupant support comprising: a moisture responsive sensor in a surveillance zone of the occupant support, the sensor being adapted to issue a return signal in response to an electromagnetic excitation signal; a transceiver adapted to excite the sensor with an electromagnetic signal, the transceiver being integrated into the occupant support.

Clause 902. The system of clause 901 including a processor adapted to receive the return signal and to issue an output based on a relationship between the return signal and the excitation signal Clause 903. The system of clause 901 wherein the processor is a component of the transceiver.

Clause 904. The system of clause 901 wherein the integrated transceiver is integrated into a bed frame.

Clause 905. The system of clause 901 wherein the integrated transceiver is integrated into a mattress portion of the bed.

Clause 906. The system of clause 901 wherein the sensor is an RFID tag.

Clause 907. The system of clause 901 wherein the sensor is in the form of a sticker.

Clause 908. The system of clause 901 wherein the sensor is installed on a pad.

Clause 909. The system of clause 901 wherein the transceiver is adapted for communication with a facility information network 138.

Clause 910. The system of clause 901 wherein the transceiver includes an antenna which loops around the sensor.

Clause 911. The system of clause 910 wherein the antenna is selected from the group consisting of metal thread and conductive ink.

Fluid Reservoir (Absorbent or Dissolving)

Clause 1001. A moisture detection apparatus comprising: a deposition layer having an exposed side susceptible to moisture contamination and a nonexposed side; a moisture sensor having a moisture responsive element separated from the deposition layer by a reservoir material.

Clause 1002. The apparatus of clause 1001 wherein the reservoir material is adjacent the nonexposed side of the deposition layer.

Clause 1003. The apparatus of clause 1001 including a base layer, at least a portion of which is spaced from the deposition layer such that the reservoir material is between the base layer and the deposition layer.

Clause 1004. The apparatus of clause 1001 wherein the reservoir material is a reservoir layer and the sensor resides within the reservoir layer.

Clause 1005. The apparatus of clause 1004 including a base layer and wherein the reservoir layer is between the base layer and the deposition layer and the moisture responsive element faces toward the deposition layer.

Clause 1006. The apparatus of clause 1004 including a base layer and wherein the reservoir layer is between the base layer and the deposition layer and the moisture responsive element faces toward the base layer.

Clause 1007. The apparatus of clause 1001 wherein the reservoir material is localized and the sensor is encapsulated in the reservoir material.

Clause 1008. The apparatus of clause 1007 wherein the reservoir material forms a pocket to encapsulate the sensor.

Clause 1009. The apparatus of clause 1007 wherein the reservoir material is a coating which encapsulates the sensor.

Clause 1010. The apparatus of clause 1001 wherein the reservoir material is a coating over at least the moisture responsive element of the sensor.

Clause 1011. The apparatus of clause 1001 wherein the reservoir material is a lining.

Clause 1012. The apparatus of clause 1001 wherein the reservoir material is an absorbent material which retards migration of fluid from a fluid deposition site to the sensor element.

Clause 1013. The apparatus of clause 1001 or 1011 wherein the reservoir material is a woven textile.

Clause 1014. The apparatus of clause 1011 wherein the woven textile is selected from the group consisting of polyester, cotton and polyamide.

Clause 1015. The apparatus of clause 1001 wherein the reservoir material is a material which dissolves when exposed to moisture thereby retarding migration of the moisture from a fluid deposition site to the sensor element until dissolution of the material is complete enough to expose the sensor element to the fluid.

Clause 1016. The apparatus of clause 1001 or 1015 wherein the reservoir material is a polymer with the chemical formula: —$(CH_2—CHOR)_n$— where R is —H or —$COCH_3$.

Clause 1017. The apparatus of clause 1001 or 1015 wherein the reservoir material has the chemical formula: —$(CH_2—CHOR)_n$— where R is —H or —$COCH_3$.

Directional Architecture—Capillary.

Clause 1101. A moisture handling apparatus comprising a sheet of material having a capillary property for encouraging moisture migration from a source to a destination.

Clause 1102. The apparatus of clause 1101 comprising capillary tubes which impart the capillary property.

Clause 1103. The apparatus of clause 1101 comprising capillary fibers which impart the capillary property.

Clause 1104. The apparatus of clause 1101 wherein the capillary property is spatially arranged so as to encourage moisture migration from a source zone to a destination zone.

Clause 1105. The apparatus of clause 1104 wherein the apparatus extends laterally and longitudinally and the capillary property is arranged to define one or more capillary pathways extending substantially exclusively laterally from the source zone to the destination zone.

Clause 1106. The apparatus of clause 1104 wherein the apparatus extends laterally and longitudinally and the capillary property is arranged to define one or more capillary pathways extending both laterally and longitudinally from the source zone to the destination zone.

Clause 1107. The apparatus of clause 1104 wherein the capillary property is arranged to define one or more capillary pathways extending radially from the source zone to the destination zone.

Clause 1108. The apparatus of clause 1104 wherein the source zone is an inboard zone and the destination zone is an outboard zone.

Clause 1109. The apparatus of clause 1104 wherein the source zone is an outboard zone and the destination zone is an inboard zone.

Clause 1110. The apparatus of clause 1101 wherein the destination zone includes a sensor responsive to the moisture.

Clause 1111. The apparatus of clause 1110 wherein the sensor is an RFID technology sensor.

Clause 1112. The apparatus of clause 1101 wherein the destination zone includes an indicator responsive to the moisture.

Clause 1113. The apparatus of clause 1101 wherein the destination zone includes a collector for collecting the migrated moisture.

Clause 1114. The apparatus of clause 1101 wherein the destination zone is a collector for collecting the migrated moisture.

Clause 1115. The apparatus of clause 1101 wherein the sheet of material is a microfiber.

Clause 1116. The apparatus of clause 1115 wherein the microfiber sheet comprises microfibers having a lineic mass of less than about 1 g/10 km.

Clause 1117. The apparatus of clause 1115 wherein the microfiber sheet comprises microfibers which have a diameter of less than about 9 micrometers.

Clause 1118. The apparatus of clause 1115 wherein the microfiber sheet comprises microfibers having a lineic mass of less than about 1 g/10 km and a diameter of less than about 9 micrometers.

Clause 1119. A system comprising the apparatus of clause 1101 and also comprising a sensor at the destination and a processor for processing information from the sensor.

Directional Architecture—Hydroaffinity.

Clause 1201. A moisture handling apparatus comprising a sheet of material having a hydroaffinity property for encouraging moisture migration from a source to a destination.

Clause 1202. The apparatus of clause 1201 wherein the hydroaffinity property is spatially arranged so as to encourage moisture migration from a source zone to a destination zone.

Clause 1203. The apparatus of clause 1202 wherein the apparatus extends laterally and longitudinally and the hydroaffinity property is arranged to define one or more fluid migration pathways extending substantially exclusively laterally from the source zone to the destination zone.

Clause 1204. The apparatus of clause 1202 wherein the apparatus extends laterally and longitudinally and the hydroaffinity property is arranged to define one or more fluid migration pathways extending both laterally and longitudinally from the source zone to the destination zone.

Clause 1205. The apparatus of clause 1202 wherein the hydroaffinity property is arranged to define one or more fluid migration pathways extending radially from the source zone to the destination zone.

Clause 1206. The apparatus of clause 1202 wherein the source zone is an inboard zone and the destination zone is an outboard zone.

Clause 1207. The apparatus of clause 1202 wherein the source zone is an outboard zone and the destination zone is an inboard zone.

Clause 1208. The apparatus of clause 1202 wherein the hydroaffinity property is arranged to be more hydrophobic at the source zone and more hydrophilic at the destination zone.

Clause 1209. The apparatus of clause 1201 wherein the destination zone includes a sensor responsive to the moisture.

Clause 1210. The apparatus of clause 1209 wherein the sensor is an RFID technology sensor.

Clause 1211. The apparatus of clause 1201 wherein the destination zone includes an indicator responsive to the moisture.

Clause 1212. The apparatus of clause 1201 wherein the destination zone includes a collector for collecting the migrated moisture.

Clause 1213. The apparatus of clause 1201 wherein the destination zone is a collector for collecting the migrated moisture.

Clause 1214. A system comprising the apparatus of clause 1201 and also comprising a sensor at the destination and a processor for processing information from the sensor.

Visual Indicators—Color Changing.

Clause 1301. A moisture detecting system comprising a sheet of material adapted to change color in response to the presence of moisture; a camera for observing the color change or lack thereof and a controller for issuing a response to the color change.

Clause 1302. The system of clause 1301 wherein an indicator portion of the sheet of material is adapted to change color in response to the presence of moisture and a transport portion is adapted to transport moisture from a site of deposition thereof to the indicator portion.

Clause 1303. The system of clause 1302 wherein the indicator portion is a perimetral portion.

Clause 1304. The system of clause 1302 wherein the indicator portion is an edge portion along a lateral side of the sheet.

Visual Indicators—UV from any Source, Plus Camera.

Clause 1401 A moisture detecting system comprising: a sheet of material which receives the moisture; a source of ultraviolet radiation adapted to expose at least a target portion of the sheet of material to the ultraviolet radiation; and a camera for observing emission of radiation or lack thereof in response to the presence of moisture within the target region and excitation of the moisture by the ultraviolet radiation; and a controller for responding to the observation.

Clause 1402. The system of clause 1401 wherein the source of ultraviolet radiation includes a light tube that extends through the sheet.

Clause 1403. The system of clause 1401 wherein the controller periodically activates and deactivates the source of ultraviolet radiation.

Clause 1404. The system of clause 1401 wherein the sheet of material is chemically treated to intensify the radiated emission.

Visual Indicators—UV from Light Tube.

Clause 1501 A moisture detecting system comprising: a sheet of material which receives the moisture; a source of ultraviolet radiation adapted to expose at least a target portion of the sheet of material to the ultraviolet radiation, the source comprising an ultraviolet radiation generator and a light tube that extends through the sheet for distributing the ultraviolet radiation to the target region.

Clause 1502. The system of clause 1501 comprising a camera for observing emission of radiation or lack thereof in response to the presence of moisture within the target region and excitation of the moisture by the ultraviolet radiation; and a controller for responding to the observation.

Clause 1503. The system of clause 1501 comprising a controller which periodically activates and deactivates the source of ultraviolet radiation.

Clause 1504. The system of clause 1501 wherein the sheet of material is chemically treated to intensify the radiation emitted in response to the presence of moisture within the target region and excitation of the moisture by the ultraviolet radiation.

Multifunctional Sensor Pad.

Clause 1601. A sensor pad comprising: at least one RFID tag, the tag including a processor adapted to process inputs obtained from multiple sensors having disparate sensing capabilities.

Clause 1602. The pad of clause 1601 wherein at least one of the sensors is a moisture sensor.

Clause 1603. The pad of clause 1601 wherein the RFID tag or tags has a mode of operation indicative of moisture and wherein at least one of the sensors senses a parameter other than moisture.

Clause 1604. The pad of clause 1601 wherein the multiple sensors have sensing capabilities selected from the group consisting of moisture, odor, chemical identity identification, chemical property identification, interface pressure, vital signs of a patient associated with the pad, and sound.

Clause 1605. The pad of clause 1601 wherein the multiple sensors are selected from the group consisting of an accelerometer, a piezoelectric device, a piezoresistive device, a vibration sensor, a capacitive sensor, an inductive sensor and a resistive sensor.

Sensor/Switch Closed by Dissolution of Insulator.

Clause 1701. A sensor comprising a switch having a first terminal, a second terminal, an electrically conductive bridge for establishing an electrical connection between the terminals when the bridge contacts the terminals, and a fuse having an open state in which the fuse impedes the establishment of the electrical connection and a closed state in which the fuse enables the establishment of the electrical connection in response to a stimulus acting on the fuse.

Clause 1702. The sensor of clause 1701 wherein the fuse includes an insulator for impeding the establishment of the electrical connection, the insulator being dissolvable in response to the presence of urine thereon.

Clause 1703. The sensor of clause 1701 wherein the stimulus is the presence of urine on the fuse.

Sensor Mat with Sensor/Switch Closed by Dissolution of Insulator.

Clause 1801. A sensor mat comprising: a sensor comprising a switch having a first terminal, a second terminal, an electrically conductive bridge for establishing an electrical connection between the terminals when the bridge contacts the terminals, and a fuse having an open state in which the fuse impedes the establishment of the electrical connection and a closed state in which the fuse enables the establishment of the electrical connection in response to a stimulus acting on the fuse; a battery; and a load; the switch being connected to the load and to the battery, the battery also being connected to the load.

Clause 1802. A sensor mat comprising: a sensor comprising a switch having a first terminal, a second terminal, an electrically conductive bridge for establishing an electrical connection between the terminals when the bridge contacts the terminals, and a fuse having an open state in which the fuse impedes the establishment of the electrical connection and a closed state in which the fuse enables the establishment of the electrical connection in response to a stimulus acting on the fuse; and a battery; the switch being connected to the battery, the switch being connectable to a load; and the battery also being connectable to the load.

Clause 1803. A sensor mat comprising: a sensor comprising a switch having a first terminal, a second terminal, an electrically conductive bridge for establishing an electrical connection between the terminals when the bridge contacts the terminals, and a fuse having an open state in which the fuse impedes the establishment of the electrical connection and a closed state in which the fuse enables the establishment of the electrical connection in response to a stimulus acting on the fuse, the switch being connectable to a battery and to a load.

Clause 1804. The sensor of clauses 1801, 1802 or 1803 wherein the load is an alarm.

RFID with Antenna Segments United by Dissolution of Insulator.

Clause 1901. A sensor comprising an RFID tag, the tag including at least two antenna segments, a bridge adapted to unite the segments, and a separator which is transitionable between a first state in which the separator impedes unification of the segments and a second state in which the separator does not impede unification of the segments, transition from the first state to the second state being in response to an agent acting on the separator.

Clause 1902. The sensor of clause 1901 wherein the agent is the presence of urine in contact with the separator.

Clause 1903. The sensor of clause 1901 wherein the agent is urine in contact with the separator and the separator is adapted to dissolve in response to urine being in contact with the separator.

Clause 1904. The sensor of clause 1901 comprising a processor.

Clause 1905. The sensor of clause 1901 comprising an adjunct sensor in communication with the processor.

While certain features have been described in the context of certain illustrative embodiments, it should be understood that such features may be adopted or applied to any of the disclosed embodiments or to other embodiments.

We claim:

1. An incontinence detection apparatus for use on a patient bed, the incontinence detection apparatus comprising
    an incontinence detection pad for placement beneath a patient on the patient bed such that the patient lies on the incontinence detection pad without wearing the incontinence detection pad, the incontinence detection pad having a substrate, at least one sensor situated on the substrate, and at least one passive RFID tag that is coupled to the at least one sensor, the passive RFID tag being configured to transmit data via an antenna contained within a boundary of the RFID tag in response to being interrogated, wherein the sensor comprises a moisture detection sensor that extends from the RFID tag beyond a boundary of the RFID tag to detect moisture on the substrate at a position spaced from the RFID tag, the sensor having interdigitated segments that are spaced apart in an open circuit configuration in the absence of moisture and that form a closed circuit configuration in response to moisture bridging between the interdigitated segments for electrical current flow, wherein the incontinence detection pad includes a plurality of substantially parallel fluid migration pathways,
    at least one antenna for emitting energy to interrogate the passive RFID tag of the incontinence detection pad, and
    circuitry coupled to the at least one antenna and providing energy to the antenna to interrogate the passive RFID tag, wherein the circuitry processes the data received from the passive RFID tag by the at least one antenna and initiates a displacement alert if the incontinence detection pad is determined to have shifted so as to be out of position on the patient bed.

2. The incontinence detection apparatus of claim 1, wherein the displacement alert is initiated if the received signal strength of the data transmitted by the passive RFID tag and received by the at least one antenna is below a threshold signal strength.

3. The incontinence detection apparatus of claim 2, wherein the at least one antenna comprises at least two antennae and further comprising a multiplexer coupled to the at least two antennae to control which of the at least two antennae is to interrogate the passive RFID tag at any given time.

4. The incontinence detection apparatus of claim 3, wherein the at least two antennae are spaced apart to define two surveillance zones.

5. The incontinence detection apparatus of claim 4, wherein the displacement alert is initiated if the received signal strength of the data transmitted by the passive RFID tag and received by each of the at least two antennae is below a threshold signal strength.

6. The incontinence detection apparatus of claim 5, wherein the displacement alert is not initiated if the received signal strength of the data transmitted by the passive RFID tag and received by at least one of the at least two antennae is above the threshold signal strength.

7. The incontinence detection apparatus of claim 1, wherein the RFID tag includes a pad antenna that receives energy from the at least one antenna coupled to the circuitry.

8. The incontinence detection apparatus of claim 1, wherein the data transmitted by the passive RFID tag includes data indicating whether the incontinence detection pad is wet or dry.

9. The incontinence detection apparatus of claim 1, wherein the at least one sensor includes at least two sensors situated on the substrate.

10. The incontinence detection apparatus of claim 1, wherein the circuitry transmits a moisture alert in response to the data indicating that the incontinence pad is wet.

11. The incontinence detection apparatus of claim 1, wherein the substrate comprises a hydrophobic material and wherein the incontinence pad comprises a moisture absorbent material overlying the interdigitated segments.

12. The incontinence detection apparatus of claim 1, wherein the circuitry is configured to control a frequency at which the at least one antenna and passive RFID tag communicate.

13. The incontinence detection apparatus of claim 1, wherein the circuitry communicates with a network of a healthcare facility.

14. The incontinence detection apparatus of claim 13, wherein the circuitry is configured to send the displacement alert to a caregiver via the network.

15. The incontinence detection apparatus of claim 14, wherein the circuitry is also configured to send a moisture alert to the caregiver via the network if the data indicates that the incontinence detection pad is wet.

16. The incontinence detection apparatus of claim 13, wherein the circuitry is configured to send the displacement alert to an electronic record for storage via the network.

17. The incontinence detection apparatus of claim 16, wherein the circuitry is also configured to send a moisture alert to the electronic record via the network if the data indicates that the incontinence detection pad is wet.

18. The incontinence detection apparatus of claim 13, wherein the circuitry is configured for wireless communication with the network.

* * * * *